United States Patent
Castejon Semidey

(10) Patent No.: US 11,944,649 B2
(45) Date of Patent: Apr. 2, 2024

(54) COMPOSITIONS AND METHODS FOR TREATMENT OF AUTISM SPECTRUM DISORDER

(71) Applicants: Immunotec Inc., Québec (CA); Ana Maria Castejon Semidey, Weston, FL (US)

(72) Inventor: Ana Maria Castejon Semidey, Weston, FL (US)

(73) Assignee: IMMUNOTEC INC., Vaudreuil-Dorion (CA)

( * ) Notice: Subject to any disclaimer, the term of this patent is extended or adjusted under 35 U.S.C. 154(b) by 456 days.

(21) Appl. No.: 16/634,946

(22) PCT Filed: Jul. 31, 2018

(86) PCT No.: PCT/US2018/044532
§ 371 (c)(1),
(2) Date: Jan. 29, 2020

(87) PCT Pub. No.: WO2019/027974
PCT Pub. Date: Feb. 7, 2019

(65) Prior Publication Data
US 2020/0206270 A1  Jul. 2, 2020

Related U.S. Application Data

(60) Provisional application No. 62/599,079, filed on Dec. 15, 2017, provisional application No. 62/539,069, filed on Jul. 31, 2017.

(51) Int. Cl.
*A61K 35/20* (2006.01)
*A61K 38/01* (2006.01)
*A61P 25/00* (2006.01)

(52) U.S. Cl.
CPC .......... *A61K 35/20* (2013.01); *A61K 38/018* (2013.01); *A61P 25/00* (2018.01)

(58) Field of Classification Search
CPC .................................................. A61K 35/20
See application file for complete search history.

(56) References Cited

FOREIGN PATENT DOCUMENTS

| WO | 2015/086789 | 6/2015 |
| WO | 2018/057514 | 3/2018 |

OTHER PUBLICATIONS

Kern (Oral Tolerability of Cysteine-Rich Whey Protein Isolate in Autism-A Pilot Study, JANA vol. 11, No. 1, 2008). (Year: 2008).*
Cassidy, A. (2013). Autism Behavior Checklist. in: Volkmar, F.R. (eds) Encyclopedia of Autism Spectrum Disorders. Springer, New York, NY. https://doi.org/10.1007/978-1-4419-1698-3_1367) (Year: 2013).*
CUP (Community-University Partnership for the Study of Children, Youth, and Families (2011). Review of the Vineland Adaptive Behavior Scales-Second Edition (Vineland-II). Edmonton, Alberta, Canada). (Year: 2011).*
International Search Report and Written Opinion of the International Searching Authority, dated Oct. 17, 2018 in International Patent Application No. PCT/US2018/044532.
Anonymous: "Immunocal for autism", www.immunocal.com, Nov. 26, 2016, pp. 1-4, XP002785177.
Al-Ayadhi et al., "Camel Milk as a Potential Therapy as an Antioxidant in Autism Spectrum Disorder (ASD)", Evidence-Based Complementary and Alternative Medicine, 2013: 1-8 (2013).
Ozturk et al., "Oxidative Imbalance in Children and Adolescents With Autism Spectrum Disorder", Bulletin of Clinical Psychopharmacology, 26(3): 257-264 (2016).
Song et al., "Cysteine-rich whey protein isolate (Immunocal) ameliorates deficits in the GFAP.HM0X1 mouse model of schizophrenia", Free Radical Biology and Medicine, 110: 162-175 (2017).

* cited by examiner

*Primary Examiner* — Terry A McKelvey
*Assistant Examiner* — Jacob A Boeckelman
(74) *Attorney, Agent, or Firm* — Wenderoth, Lind & Ponack, L.L.P.

(57) ABSTRACT

Provided herein are compositions, uses thereof, and methods for treating Autism or Autism Spectrum Disorder (ASD) in a subject in need thereof, wherein the compositions comprise a whey protein isolate and/or whey protein concentrate.

4 Claims, 6 Drawing Sheets

Change in Vineland Adaptive Behaviour Scale Scores in Non-Responder and Responder Groups

COMPOSITIONS AND METHODS FOR TREATMENT OF AUTISM SPECTRUM DISORDER

FIELD OF INVENTION

The present invention relates generally to the treatment of autism spectrum disorder (ASD). More specifically, the present invention relates to compositions and methods for treating and/or preventing and/or ameliorating symptoms of ASD and/or managing autism and related conditions.

BACKGROUND

Autism Spectrum Disorders (ASD) are commonly associated with behavioural characteristics including limited social interaction, lack of verbal communication, and/or narrow and repetitive behaviour patterns. Autism is one of the fastest growing developmental disorders in the US, with an estimated 1 to 1.5 million Americans being affected. The incidence of ASD is estimated at about 1 in 68 children, with boys being approximately four times more likely than girls to have autism. Currently, techniques for medical detection of autism are lacking, and there is no known cure.

Autism is a complex neurodevelopmental disorder that affects 1 in 68 children in the United States, with four times as many males diagnosed than females (Christensen et al. 2016; CDC 2016). The spectrum of impairments noted in this disorder have coined the umbrella term "Autism Spectrum Disorder" (ASD). The fifth edition of the Diagnostic and Statistical Manual of Mental Disorders (DSM-V) defines ASD as having "deficits in social interaction and communication together with restricted and repetitive behaviors and interests" (American Psychiatric Association, 2013). Clinical symptoms are used to diagnose children with autism around onset at age three; a myriad of behavioral assessments are utilized for autism diagnostic purposes with the Autism Diagnostic Observation Schedule (ADOS) (Lord et al. 1989; 2000) as the standard. Despite extensive research, no definite aid for diagnosis or treatment has been detected (Loke, Hannan, and Craig 2015). Early intervention programs and special schooling are the most effective for those with this neurodevelopmental disorder and although outcomes of early intervention vary, all children benefit (Alabdali, Al-Ayadhi, and El-Ansary 2014). A combination of applied behavioral analysis (ABA) along with other educational, developmental, occupational and speech therapies are common in affected children with limited results (Frye et al. 2017). The need for other effective treatments for core symptoms of autism is highly sought after.

Autism was first documented as a mental disorder in 1980 and still its exact etiology is undetermined. The heterogeneity of ASD can be observed in the neurologic, metabolic, and immunologic systems. Therefore, it is speculated to be a multi-factorial disorder, involving epigenetics, genetics and environmental factors.

Oxidative stress has been associated with a number of diseases/disorders in humans. Oxidative stress may play a role in ASD, and some research has focused on changes to the methionine-glutathione transsulfuration pathway (James, S. J., et al., 2006, American Journal of Medical Genetics Part B (Neuropsychiatric Genetics), 141B: 947-956).

Glutathione deficiency has been observed in plasma of children with autism (GSH (µmol/L): 7.6+/−1.4 in control versus ASD; Oxidized Glutathione (nmol/L): 0.32+/−0.1 in control versus 0.55+/−0.2 in ASD; GSH:GSSG Ratio: 25.5+/−8.9 in control versus 8.6+/−3.5 in ASD). Previous studies have suggested that children with autism may have an increased susceptibility to oxidative stress, be it environmental, intracellular, or both (James et al., 2004; 2006; 2009; Melynk et al., 2012; Rose et al., 2012; Frye et al., 2013). Further, impaired methylation capacity may be linked to development and/or clinical manifestation of autism disorder.

Anecdotal reports and public opinion suggested that non-denatured whey protein isolate might be problematic for children with autism due to the presence of cysteine and other sulfurated amino acids. To better examine the tolerability of non-denatured whey protein isolate in children with autism, Kern et al. (Oral Tolerability of Cysteine-Rich Whey Protein Isolate in Autism—A Pilot Study, JANA, 11(1), 2008, 36-41; herein incorporated by reference in its entirety) performed a study which suggested that non-denatured whey protein isolate (in this case, Immunocal®) may be used without high rates of side effects. While this study suggested that non-denatured whey protein isolate may be safe and may have acceptable tolerability in children with autism or ASD, the primary endpoint examined was limited to tolerability. These studies were not sufficient to obtain statistically significant insights on changes in behavioural parameters or condition improvement. The data collected were insufficient for statistical analysis. Kern et al. indicate that caution should be used in interpreting the limited behavioural data. Accordingly, the effects of non-denatured whey protein isolate on GSH levels and behaviour in children with autism or ASD remained unknown.

Alternative, additional, and/or improved compositions and methods for the treatment of autism spectrum disorders, and particular traits or symptoms thereof, are desirable.

SUMMARY OF INVENTION

It has now been found that treatment with a composition comprising whey protein isolate and/or whey protein concentrate may be used for treating autism in a subject in need thereof. Studies described in detail herein indicate that treatment with a composition comprising whey protein isolate and/or whey protein concentrate, such as Immunocal®, may be used to improve subject scores on autism assessment measures such as Vineland (such as Vineland Adaptive Behaviour Score), CARS, SCQ, CBCL, and/or ADI-R. In certain embodiments, such improvements may include, but are not limited to, autism severity, verbal communication, developmental status, and/or behaviour issues such as emotional reactions.

In an embodiment, there is provided herein a method for treating Autism or Autism Spectrum Disorder (ASD) in a subject in need thereof, said method comprising:
  administering a composition comprising whey protein isolate and/or whey protein concentrate to the subject.

In another embodiment, there is provided herein a method for treating, preventing, or ameliorating symptoms of Autism or Autism Spectrum Disorder (ASD) in a subject in need thereof, said method comprising:
  administering a composition comprising whey protein isolate and/or whey protein concentrate to the subject.

In yet another embodiment, there is provided herein a use of a composition for treating Autism or Autism Spectrum Disorder (ASD) in a subject in need thereof, said composition comprising whey protein isolate and/or whey protein concentrate.

In still another embodiment, there is provided herein a use of a composition for treating, preventing, or ameliorating symptoms of Autism or Autism Spectrum Disorder (ASD) in a subject in need thereof, said composition comprising whey protein isolate and/or whey protein concentrate.

In yet another embodiment, there is provided herein a use of a composition for manufacturing a medicament for treating Autism or Autism Spectrum Disorder (ASD) in a subject in need thereof, said composition comprising whey protein isolate and/or whey protein concentrate.

In yet another embodiment, there is provided herein a use of a composition for manufacturing a medicament for treating, preventing, or ameliorating symptoms of Autism or Autism Spectrum Disorder (ASD) in a subject in need thereof, said composition comprising whey protein isolate and/or whey protein concentrate.

In another embodiment, there is provided herein a composition for treating Autism or Autism Spectrum Disorder (ASD) in a subject in need thereof, said composition comprising whey protein isolate and/or whey protein concentrate.

In yet another embodiment, there is provided herein a composition for treating, preventing, or ameliorating symptoms of Autism or Autism Spectrum Disorder (ASD) in a subject in need thereof, said composition comprising whey protein isolate and/or whey protein concentrate.

In certain further embodiments, the whey protein isolate and/or whey protein concentrate may be provided at about 0.5 g/kg for subjects having less than 18 kg of body weight, or at about 10 g/day for subjects over 18 kg body weight.

In further embodiments, treatment with the whey protein isolate and/or whey protein concentrate may provide an increase in tGSH levels, GSH levels, or both.

In yet another embodiment, treatment with the whey protein isolate and/or whey protein concentrate may improve at least one core behavioural area in autism or ASD. In certain embodiments, treatment with the whey protein isolate and/or whey protein concentrate may improve at least one of Vineland, CARS, SCQ, CBCL, or ADI-R scores in the subject. In certain embodiments, treatment may impact areas of autism severity, verbal communication, expressive communication, personal daily living skills, coping skills, or socialization, for example.

In still another embodiment, treatment with the whey protein isolate and/or whey protein concentrate may improve Vineland Adaptive Behaviour Scores in the subject.

In certain embodiments, the subject may be a subject which has low levels of GSH or tGSH. In certain embodiments, the subject may be a subject which has high levels of GSH or tGSH. In certain embodiments, the subject may be a subject which has intermediate levels of GSH or tGSH.

In still another embodiment, the subject may be a child.

In yet another embodiment, the whey protein isolate and/or whey protein concentrate may comprise Immunocal®, or a functional equivalent thereof.

In still another embodiment, the composition may further comprise a pharmaceutically acceptable excipient, carrier, or diluent.

In yet another embodiment, the whey protein isolate and/or whey protein concentrate may be substantially undenatured.

In still a further embodiment, the Autism Spectrum Disorder (ASD) may comprise autism, Asperger syndrome, pervasive developmental disorder not otherwise specified (PDD-NOS), Childhood Disintegrative Disorder, syndromic autism or autism of known etiology such as fragile X syndrome, PTEN macrocephaly syndrome, RETT syndrome, tuberous sclerosis complex, Timothy syndrome, and/or Joubert syndrome.

In still another embodiment, treatment with the whey protein isolate and/or whey protein concentrate may provide behavioural improvement in the subject.

In yet another embodiment, treatment with the whey protein isolate and/or whey protein concentrate may provide behavioural improvement in the subject in terms of autism severity, verbal communication, expressive communication, personal daily living skills, coping skills, socialization, or any combination thereof.

In another embodiment, treatment with the whey protein isolate and/or whey protein concentrate may increase a tGSH level, a GSH level, or both, in the subject.

In still another embodiment, the subject may be a subject which has been identified as being a responder to treatment with the composition. In certain embodiments, the subject may be about 4.0 years of age, 4.1 years of age, 4.2 years of age, 4.3 years of age, 4.4 years of age, or 4.5 years of age. In certain embodiments, the subject may be about 4.23±0.22 years old. In certain embodiments, the subject may be a subject having a relatively higher baseline level of plasma and/or intracellular GSH, tGSH, or both, as compared to other children with autism. In certain embodiments, responders may be identified as children with autism or ASD with lower plasma and/or intracellular levels of GSH, tGSH, or both, when compared to children without a diagnosis of autism. In certain embodiments, the subject may be a subject having a baseline intracellular level of GSH, tGSH, or both, when compared to children without a diagnosis of autism (it has previously been found that plasma, intracellular, and even brain levels of GSH may be decreased compared to control children without autism; see Background section and Example 1 discussion) of about 100-150 nM/$10^5$ WBC, or about 127.8±19.8 nM/$10^5$ WBC, or about 127.8 nM/$10^5$ WBC, as measured by the Tietze method, for example. In certain embodiments, a responder may be considered as a subject for which treatment as described herein provides equal to or more than about 2 points, or about 1 standard deviation, in the VABS-II composite scores. In certain embodiments, a responder may be considered as a subject for which treatment as described herein provides for improvement in one or more VABS-II domains/sub-domains such as: communication score, receptive V-scale score, expressive v-scale score, daily living skills, or personal v-scale score.

Accordingly, in certain embodiments, the subject in need thereof may be a subject identified as being a responder based on:

[1] the subject having autism or ASD and having lower plasma and/or intracellular levels of GSH, tGSH, or both, as compared to a control group without a diagnosis of autism or ASD; or

[2] the subject having autism or ASD and having higher plasma and/or intracellular levels of GSH, tGSH, or both, as compared to a control group with a diagnosis of autism or ASD; or both [1] and [2].

In certain embodiments, the subjects and control groups may be children.

In another embodiment, there is provided herein a method for improving one or more behavioural traits which are assessed by one or more of:

CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score, in a subject in need thereof having autism or ASD, said method comprising:

administering a composition comprising whey protein isolate and/or whey protein concentrate to the subject.

In another embodiment, there is provided herein a use of a whey protein isolate and/or whey protein isolate for improving one or more behavioural traits which are assessed by one or more of:

CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score, in a subject in need thereof having autism or ASD. In certain embodiments, the above methods and uses may include an initial step of identifying a subject in need of treatment based on the subject having impairment in one or more behavioural traits which are assessed by one or more of:

CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

BRIEF DESCRIPTION OF DRAWINGS

These, and other features and aspects, of the present invention will become further understood with regard to the following description and accompanying Figures, wherein.

* p<0.05 indicates that a statistically significant difference does exist.

DETAILED DESCRIPTION

Described herein are compositions and methods for the treatment of autism spectrum disorder. It will be appreciated that embodiments and examples are provided for illustrative purposes intended for those skilled in the art, and are not meant to be limiting in any way.

The Glutathione (GSH)/Glutathione Disulfide (GSSG) redox equilibrium is believed to regulate nitrogen and oxygen free radical scavenging; protein redox status and enzyme activity; cell membrane integrity and signal transduction; transcription factor binding and gene expression; phase II detoxification; and apoptosis (Dickinson, Moellering, et al., 2003; Klatt and Lamas, 2000; Dickinson and Forman, 2002; and Deplancke and Gaskins, 2002).

There is genetic evidence of oxidative stress, with relevant genes encoding for/potentially associated with oxidative stress in autistic children including: Reduced folate carrier (RFC 80G>A); Transcobalamin II (TCN2 776G>C); Catechol-O-methyltransferase (COMT 472G >A); Methylenetetrahydrofolate reductase (MTHFR 677C>T and 1298A>C); and Glutathione-S-Transferase (GST M1) (James, Melnyk et al., 2006). Lyphoblastoid cell line studies have previously observed the following information (see Table A).

TABLE A

| Previous Lymphoblastoid Cell Line Studies | | | |
|---|---|---|---|
| Autistic LCL (Autism Genetic Repository Exchange) | Age | Control LCL (Corriel Cell Repository) | Age |
| AU3964302 | 3.8 | GM09659 | 4 |
| AU1157303 | 3.1 | GM08336 | 3 |
| AU055104 | 5 | GM11898 | 5 |
| AU2140305 | 5.9 | GM09380 | 6 |
| AU3907302 | 4.4 | GM09659 | 4 |
| AU3912302 | 4.9 | GM11898 | 5 |

Figure 1:
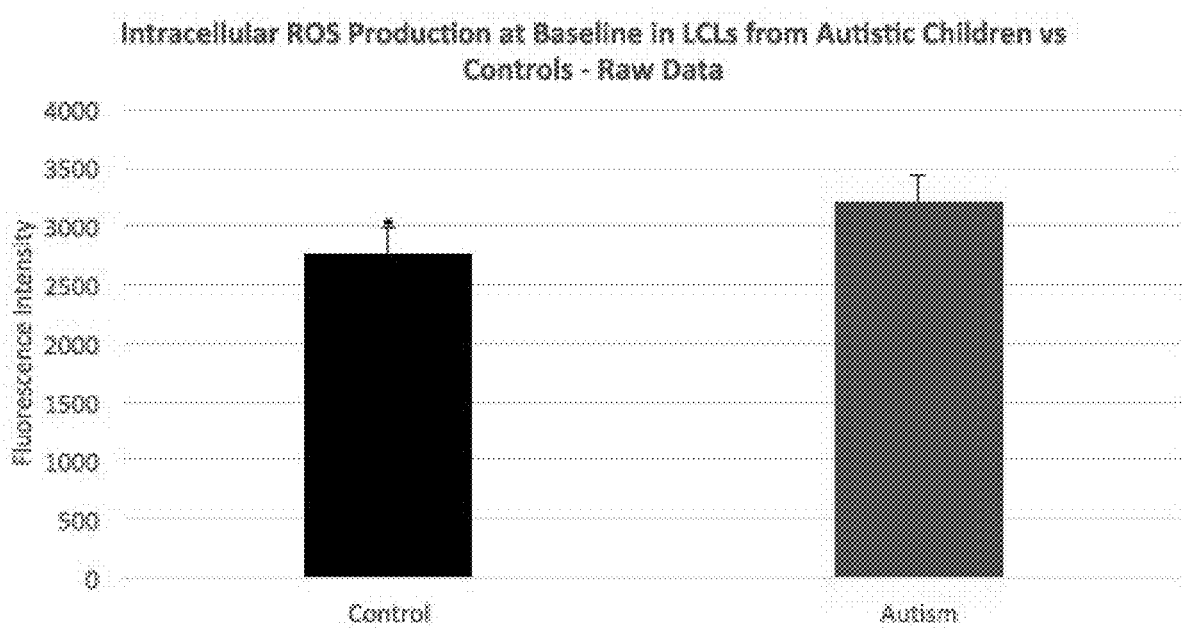
FIG. 1 shows higher reactive oxygen species (ROS) (free radicals) at baseline in lymphoblastoid cell lines (LCLs) from children with Autism.
Figure 2:
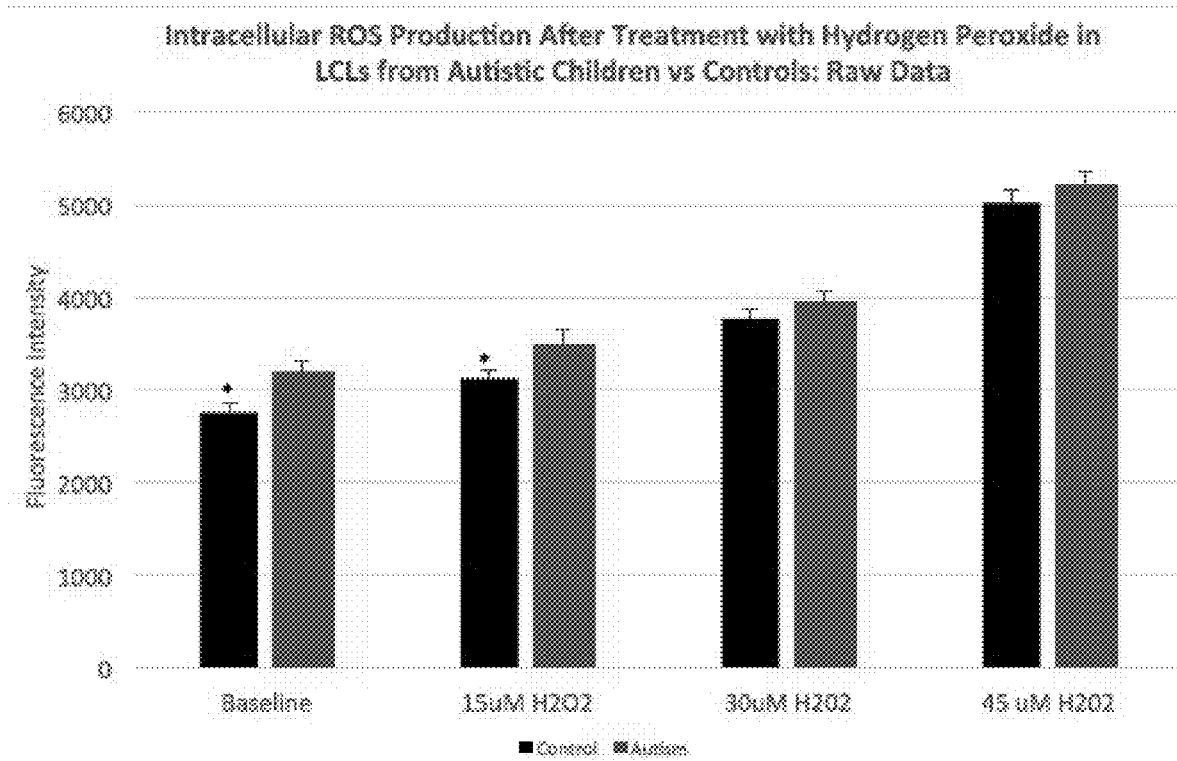
FIG. 2 shows intracellular reactive oxygen species (ROS) production after treatment with hydrogen peroxide in LCLs from Autistic children versus controls.

Higher reactive oxygen species (ROS) at baseline in LCLs from children with Autism has been observed (see FIG. 1). Intracellular ROS production after treatment with hydrogen peroxide (i.e. exposure to oxidative stress) in LCLs from Autistic children versus controls is shown in FIG. 2.

It has been previously observed that children with autism may have lower GSH levels, and may be more vulnerable to oxidative stress. The present inventors hypothesized that improving glutathione levels may at least partially protect or ameliorate those with autism from at least one negative effect of high oxidative stress, and therefore may prevent and/or improve at least one clinical manifestation of this disorder. In particular, the present inventors sought to investigate the effects of a whey protein isolate and/or whey protein concentrate on subjects with autism. Whey protein isolates and whey protein concentrates may act as glutathione precursors, by providing an enriched source of bioavailable cysteine after administration.

A study was conducted with the goal of establishing the effects of a 90 day diet supplementation with a cysteine-rich whey protein isolate (in this case, commercially available Immunocal®) on autistic behaviour. The study also sought to investigate correlation between blood glutathione levels with behavioural changes in children with autism supplemented with a cysteine-rich whey protein. Further, the study was designed to assess the tolerability of a cysteine-rich whey protein supplement (Immunocal®) in children with autism, and to note adverse effects in children, if any. The study is further described in Example 1 below.

In an embodiment, there is provided herein a method for treating Autism or Autism Spectrum Disorder (ASD) in a subject in need thereof, said method comprising:

administering a composition comprising whey protein isolate and/or whey protein concentrate to the subject.

In another embodiment, there is provided herein a method for at least partially treating, preventing, or ameliorating symptoms of Autism or Autism Spectrum Disorder (ASD) in a subject in need thereof, said method comprising:

administering a composition comprising whey protein isolate and/or whey protein concentrate to the subject.

In yet another embodiment, there is provided herein a use of a composition for treating Autism or Autism Spectrum Disorder (ASD) in a subject in need thereof, said composition comprising whey protein isolate and/or whey protein concentrate.

In still another embodiment, there is provided herein a use of a composition for at least partially treating, preventing, or ameliorating symptoms of Autism or Autism Spectrum Disorder (ASD) in a subject in need thereof, said composition comprising whey protein isolate and/or whey protein concentrate.

In yet another embodiment, there is provided herein a use of a composition for manufacturing a medicament for treating Autism or Autism Spectrum Disorder (ASD) in a subject in need thereof, said composition comprising whey protein isolate and/or whey protein concentrate.

In yet another embodiment, there is provided herein a use of a composition for manufacturing a medicament for at least partially treating, preventing, or ameliorating symptoms of Autism or Autism Spectrum Disorder (ASD) in a subject in need thereof, said composition comprising whey protein isolate and/or whey protein concentrate.

In another embodiment, there is provided herein a composition for treating Autism or Autism Spectrum Disorder (ASD) in a subject in need thereof, said composition comprising whey protein isolate and/or whey protein concentrate.

In yet another embodiment, there is provided herein a composition for at least partially treating, preventing, or ameliorating symptoms of Autism or Autism Spectrum Disorder (ASD) in a subject in need thereof, said composition comprising whey protein isolate and/or whey protein concentrate.

In certain embodiments, the subject in need thereof may be a subject having Autism or Autism Spectrum Disorder (ASD). In still further embodiments, the subject in need thereof may be a subject suspected of having, or at risk of developing, a mental disorder such as Autism or Autism Spectrum Disorder (ASD). In certain embodiments of methods and uses as described herein, an additional step of subjecting the subject to testing for determination of autism or ASD status may be performed in order to identify the subject as being in need of treatment. In certain embodiments, such a step of diagnosing the autism or ASD status of the subject may be performed prior to administering the composition comprising whey protein isolate and/or whey protein concentrate to the subject. In still further embodiments of methods and uses as described herein, an additional step of subjecting the subject to testing for determination of autism or ASD status may performed during, following, or both during and following, treatment of the subject with the composition comprising whey protein isolate and/or whey protein concentrate in order to determine effects of the treatment and/or inform whether adjustment of dosage and/or dosage regimen would be of interest moving forward.

In certain embodiments, the subject in need thereof may be a subject identified as being particularly responsive to treatment according to the methods described herein, i.e. the subject may be a "responder". In certain embodiments, the subject may be about 4 years of age, such as about 4.0 years of age, 4.1 years of age, 4.2 years of age, 4.3 years of age, 4.4 years of age, or 4.5 years of age. In certain embodiments, the subject may be about 4.23±0.22 years old. In certain embodiments, the subject may be a subject having a relatively higher baseline level of plasma or intracellular GSH, tGSH, or both, as compared to other children with autism. In certain embodiments, responders may be identified as children with autism or ASD with lower plasma or intracellular levels of GSH, tGSH, or both, when compared to children without a diagnosis of autism. In certain embodiments, the subject may be a subject having a baseline intracellular level of GSH, tGSH, or both, when compared to children without a diagnosis of autism (it has previously been found that plasma, intracellular, and even brain levels of GSH may be decreased compared to control children without autism; see Background section and Example 1 discussion) of about 100-150 nM/$10^5$ WBC, or about 127.8±19.8 nM/$10^5$ WBC, or about 127.8 nM/$10^5$ WBC, as measured by the Tietze method, for example. In certain embodiments, a responder may be considered as a subject for which treatment as described herein provides equal to or more than about 2 points, or about 1 standard deviation, in the VABS-II composite scores. In certain embodiments, a responder may be considered as a subject for which treatment as described herein provides for improvement in one or more VABS-II domains/sub-domains such as: communication score, receptive V-scale score, expressive v-scale score, daily living skills, or personal v-scale score.

In certain embodiments, the subject in need thereof may be identified as being a responder, or a subject particularly likely to benefit from treatment, based on the subject having an abnormal or poor score on at least one of the following behavioural assessments: CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

In certain embodiments, the subject in need thereof may be a subject identified as being a responder based on:

[1] the subject having autism or ASD and having lower plasma and/or intracellular levels of GSH, tGSH, or both, as compared to a control group without a diagnosis of autism or ASD; or

[2] the subject having autism or ASD and having higher plasma and/or intracellular levels of GSH, tGSH, or both, as compared to a control group with a diagnosis of autism or ASD; or both [1] and [2].

In certain embodiments, the subjects and control groups may be children.

In certain embodiments, methods and uses as described herein may include a step of identifying a subject as being a responder. Such a step may, in certain embodiments, include measuring the subject's plasma and/or intracellular level(s) of GSH, tGSH, or both, and comparing the measured level(s) to those of a suitable control group. In certain embodiments, such measurements may utilize, for example, the Tietze method (Tietze, F. (1969) Enzymatic Method for Quantitative Determination of Nanogram Amounts of Total and Oxidized Glutathione: Applications to Mammalian Blood and Other Tissues. *Analytical Biochemistry,* 27:502-522' herein incorporated by reference in its entirety).

In certain embodiments, methods and uses as described herein may include an additional step of identifying the subject as being a responder, thereby identifying the subject as being particularly responsive to treatment as described herein. In certain embodiments, such a step of identifying the subject as being a responder may be performed prior to administering the composition comprising whey protein isolate and/or whey protein concentrate to the subject (i.e. prior to treatment). In certain embodiments, such a step of identifying the subject as being a responder may be performed following administration of the composition comprising whey protein isolate and/or whey protein concentrate to the subject (i.e. post-treatment) in order to identify the subject as a candidate for a subsequent round of treatment. In certain embodiments, such a step of identifying the subject as being a responder may include determining age of the subject, determining the subject's baseline level of GSH, determining whether the subject experiences equal to or more than about 2 points or about 1 standard deviation in VABS-II composite scores following treatment, or any combination thereof.

Accordingly, in yet another embodiment, there is provided herein a method for treating Autism or Autism Spectrum Disorder (ASD) in a subject having, suspected of having, or at risk of developing, Autism or ASD, said method comprising:
  optionally, subjecting the subject to testing to determine Autism or ASD status of the subject, thereby identifying the subject as being in need of treatment;
  optionally, identifying the subject as being a responder based on age and/or baseline GSH levels;
  administering a composition comprising whey protein isolate and/or whey protein concentrate to the subject;
  optionally, subjecting the subject to testing to determine improvement in Autism or ASD status of the subject as a result of administration of the composition;
  optionally, identifying the subject as being a responder based on whether the subject experiences more than about 2 points or about 1 standard deviation in VABS-II composite scores following administration of the composition; and
  optionally, performing a subsequent administration of the composition comprising whey protein isolate and/or whey protein concentration to the subject.

In another embodiment, there is provided herein a method for at least partially treating, preventing, or ameliorating symptoms of Autism or Autism Spectrum Disorder (ASD) in a subject having, suspected of having, or at risk of developing, Autism or ASD, said method comprising:
  optionally, subjecting the subject to testing to determine Autism or ASD status of the subject, thereby identifying the subject as being in need of treatment;
  optionally, identifying the subject as being a responder based on age and/or baseline GSH levels;
  administering a composition comprising whey protein isolate and/or whey protein concentrate to the subject;
  optionally, subjecting the subject to testing to determine improvement in Autism or ASD status of the subject as a result of administration of the composition;
  optionally, identifying the subject as being a responder based on whether the subject experiences more than about 2 points or about 1 standard deviation in VABS-II composite scores following administration of the composition; and
  optionally, performing a subsequent administration of the composition comprising whey protein isolate and/or whey protein concentration to the subject.

In certain further embodiments, the whey protein isolate and/or whey protein concentrate may be provided at a dosage of about 0.5 g/kg for subjects having less than 18 kg of body weight, or at about 10 g/day for subjects over 18 kg body weight. It will be understood that these examples are not intended to be limiting, and that higher and lower dosages are also contemplated. In certain non-limiting embodiments, for example, it is contemplated that compositions as described herein may be administered orally in an amount suitable for achieving a desired effect. In certain non-limiting embodiments, compositions as described herein may be administered orally in a dosage of about 20-40 grams per day, for example, and may be administered once or more than once daily, for example. In certain embodiments, dosage for subjects about 40 lbs and under may be about 0.5 grams per kilo of body weight, for example.

In certain embodiments, the subject may be treated over a period time. By way of example, the subject may receive treatment for one or more days, one or more weeks, one or more months, or one or more years. Treatments may be administered at regular intervals, or as needed or desired based on state of the subject, for example. In certain embodiments, treatments may be administered daily, biweekly, or weekly, for example. In certain embodiments, the subject may receive treatment over a period of one or more months. For example, the subject may receive treatment for at least 3 months, or for at least about 90 days. It will be understood that a variety of treatment schedules and regimens may be possible, and that these examples are provided for illustrative, non-limiting purposes.

For reference, embodiments of contemplated dosages and/or dosage regimens are set out in Example 1 below. As will be understood, a wide variety of dosages and/or dosage regiments may be possible, and the examples provided in Example 1 are not intended to be limiting. For example, it is contemplated that dosages and/or dosage regimens may be higher and/or lower than those used in Example 1.

In further embodiments, treatment with the whey protein isolate and/or whey protein concentrate may provide an increase in tGSH levels, GSH levels, or both.

In yet another embodiment, treatment with the whey protein isolate and/or whey protein concentrate may improve at least one of Vineland, CARS, SCQ, CBCL, or ADI-R scores in the subject.

In still another embodiment, treatment with the whey protein isolate and/or whey protein concentrate may improve Vineland Adaptive Behaviour Scores in the subject.

In still another embodiment, treatment with the whey protein isolate and/or whey protein concentrate may provide behavioural improvement in the subject. In certain embodiments, treatment with the whey protein isolate and/or whey protein concentrate may provide behavioural improvement in the subject in terms of autism severity, verbal communication, expressive communication, personal daily living skills, coping skills, socialization, or any combination thereof.

In certain embodiments, treatment with the whey protein isolate and/or whey protein concentrate may provide an improvement in autism behaviour and/or severity. In certain embodiments, treatment with whey protein isolate and/or whey protein concentrate may provide an improvement in total ADI-R score. In certain embodiments, treatment with the whey protein isolate and/or whey protein concentrate may provide an improvement in ADI-R Reciprocal Social Interaction sub-score. In certain embodiments, treatment with the whey protein isolate and/or whey protein concentrate may provide an improvement in behaviour t-score of CARS.

In certain embodiments, treatment with the whey protein isolate and/or whey protein concentrate may provide an improvement in verbal communication. In certain embodiments, treatment with the whey protein isolate and/or whey protein concentrate may provide an improvement in SCQ.

In certain embodiments, treatment with the whey protein isolate and/or whey protein concentrate may provide an improvement in developmental status. In certain embodiments, treatment with the whey protein isolate and/or whey protein concentrate may provide an improvement in Vineland Adaptive behaviour composite score, communication domain, and/or socialization domain. In certain embodiments, treatment with the whey protein isolate and/or whey protein concentrate may provide an improvement in Vineland expressive communication sub-domain, personal daily living skills sub-domain, coping skills sub-domain, and/or fine motor skills sub-domain.

In certain embodiments, treatment with whey protein isolate and/or whey protein concentrate may provide an improvement in Vineland Adaptive behaviour composite score, socialization domain, and/or personal daily living skills.

In certain embodiments, treatment with the whey protein isolate and/or whey protein concentrate may provide an improvement in behavioural issues. In certain embodiments, treatment with the whey protein isolate and/or whey protein concentrate may provide an improvement in CBCL emotionally reactive t-scores.

In another embodiment, treatment with the whey protein isolate and/or whey protein concentrate may increase a tGSH level, a GSH level, or both, in the subject.

In certain embodiments, the subject may be a subject which has low levels of GSH or tGSH; intermediate levels of GSH or tGSH; or high levels of GSH or tGSH. Studies described herein indicate that improvement in behaviour was not limited GSH levels in the subject. Therefore, in certain embodiments, it is contemplated that behavioural benefits may be observed in a subject treated with whey protein isolate and/or whey protein concentrate independently of GSH or tGSH levels.

As will be understood, the subject for treatment may include any suitable subject in need of such treatment. In certain embodiments, it is contemplated that the subject is not limited to any particular age or age range, and may be, for example, an adult or a child. In particular embodiments, the subject may be a child. In certain embodiments, the child may be, for example, between ages 0-15, for example about 1, 2, 3, 4, 5, 6, 7, 8, 9, 10, 11, 12, 13, 14, or 15 years old, or any age therebetween, or any age range spanning between such ages. In certain further embodiments, the child may be from 2-8 years old, from 3-6 years old, from 3-5 years old, or about 4 years old, for example.

As will be understood, Autism Spectrum Disorder may encompass several disorders or conditions. Autism Spectrum Disorder (ASD) as referred to herein may be considered according to the Diagnostic and Statistical Manual of Mental Disorders, 5$^{th}$ Edition (DSM-5), which is herein incorporated by referenced in its entirety. As such, in certain embodiments, Autism Spectrum Disorder (ASD) may comprise autism, Asperger syndrome, pervasive developmental disorder not otherwise specified (PDD-NOS), or Childhood Disintegrative Disorder.

In certain embodiments Autism Spectrum Disorder may encompass syndromic autism or autism of known etiology. In certain embodiments, Autism Spectrum Disorder may encompass fragile X syndrome, PTEN macrocephaly syndrome, RETT syndrome, tuberous sclerosis complex, Timothy syndrome, or Joubert syndrome.

In certain embodiments, the subject in need of treatment using methods as described herein may be a subject having impairment in one or more behavioural traits which are assessed by one or more of:

CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

In certain embodiments, a responder as described herein may be defined as a subject with an abnormal score on one or more of the behavioural assessments above.

In certain embodiments, the above methods and uses may include an initial step of identifying a subject in need of treatment based on the subject having impairment in one or more behavioural traits which are assessed by one or more of:

CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

In certain further embodiments, such methods and uses may include an initial step of determining the subject's baseline CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

In yet another embodiment, the whey protein isolate and/or whey protein concentrate may be or comprise Immunocal®, or a functional equivalent thereof.

In still another embodiment, the composition may further comprise a pharmaceutically acceptable excipient, carrier, or diluent.

In yet another embodiment, the whey protein isolate and/or whey protein concentrate may be substantially undenatured.

Compositions described herein may comprise whey protein isolate and/or whey protein concentrate, which is a source of the glutathione precursor cysteine.

Compositions comprising whey protein isolate and/or whey protein concentrate may comprise any suitable composition comprising whey protein isolate and/or whey protein concentrate which may serve as a glutathione precursor by providing an enriched source of bioavailable cysteine after administration. As will be understood, whey proteins may generally be considered as a group a milk proteins which remain soluble in "milk serum" or whey after precipitation of caseins at pH 4.6 and 20° C. Major whey proteins in cow's milk, for example, may include beta-lactoglobulin (βL), alpha-lactalbumin (αL), immunoglobulin, and serum albumin (SA). The product of industrial separation of this protein mixture from whey is typically referred to as whey protein isolate (WPI; also known as whey protein concentrate, WPC).

Compositions may, optionally, additionally comprise one or more pharmaceutically acceptable excipients, diluents, and/or carriers, one or more vitamins, essential amino acids, or minerals, one or more antioxidants, one or more additional glutathione precursors, and/or one or more nutritional diet supplement components, for example.

In certain embodiments, compositions and/or medicaments as described herein may additionally comprise, or may be for use in combination (simultaneously or sequentially) with, one or more vitamins typically used in the treatment of autism and/or ASD.

Compositions may also include, and/or be used in simultaneous or sequential combination with, one or more other drugs, pharmaceutical compositions, or therapies used in the treatment or management of autism as will be known to the person of skill in the art.

In certain embodiments, compositions comprising whey protein isolate and/or whey protein concentrate may additionally comprise one or more pharmaceutically acceptable carriers, diluents, or excipients which may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disentegrants known in the art (see, for example, Remington: The Science and Practice of Pharmacy (2012); herein incorporated by reference in its entirety). Examples of pharmaceutically acceptable carriers, diluents, and excipients may be found in, for example, Remington's Pharmaceutical Sciences (2000—20th edition) and in the United States Pharmacopeia: The National Formulary (USP 40 NF35) published in 2017.

In certain embodiments, a whey protein isolate or a whey protein concentrate as described herein may include any suitable extract, isolate, concentrate, or other product which is obtainable from whey protein. As will be understood, whey protein comprises a mixture of milk proteins that remain soluble in milk serum or whey after precipitation of caseins, for example. Whey is often encountered as a by-product of cheese or casein manufacture. Major whey protein components may include, for example but without wishing to be limiting, beta-lactoglobulin, alpha-lactalbumin, immunoglobulin, and/or serum albumin. Although bovine milk is commonly used for obtaining whey protein, it will be understood that other sources of milk are also contemplated. Whey protein isolate (WPI) is generally considered in the field as having >90% protein, while whey protein concentrate (WPC) may have protein concentrations below 90%; however, for the present purposes, WPI and WPC may be considered as generally interchangeable unless otherwise explicitly specified.

In particular embodiments, a whey protein isolate or whey protein concentrate as described herein is preferably a substantially undenatured whey protein isolate or whey protein concentrate. Undenatured isolates and concentrates are those in which one or more of the protein component(s) obtainable from whey protein remain substantially undenatured (i.e. tertiary protein structure is substantially maintained and/or disulfide bonds between cysteine residues remain substantially intact) in the whey protein isolate or whey protein concentrate.

Whey proteins contain sulfur-containing amino acids such as cysteine (Cys). These Cys amino acid residues may occur as free residues (i.e. —SH; reduced), or two Cys residues may form intramolecular disulfide bonds (S—S; oxidized) so as to produce cystine dimers. Such disulfide bonds play a role in protein folding. In certain embodiments, undenatured whey protein isolates or whey protein concentrates as described herein may include those having at least about 2 wt % cystine dimer. Examples of undenatured whey protein isolates and whey protein concentrates may include those having about 2 wt % cystine dimer, or more than about 2 wt % cystine dimer. For example, the wt % of cystine dimer may be about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 wt %, or the wt % cystine dimer may fall within a range spanning between any two such values, or a range bounded at the lower end by any such value.

Whey protein isolates and whey protein concentrates may be obtained using any suitable technique(s) as will be known to the person of skill in the art having regard to the teachings herein. Such techniques may include ultrafiltration using membranes, ion exchange methods, and membrane methods, for example. Discussions of suitable techniques may be found in, for example, Advanced Dairy Chemistry, McSweeney and Mahony (Ed.), Volume 1B: Proteins: Applied Aspects, 4th Edition, Springer, ISBN: 978-1-4939-2799-9 (herein incorporated by reference in its entirety).

Examples of suitable compositions comprising whey protein isolate and/or whey protein concentrate are described in Canadian patent nos. 1,333,471, 1,338,682, 2,142,277, and 2,090,186, each of which is herein incorporated by reference in its entirety. CA 2,142,277, for example, provides detailed preparation processes and analytical characterization of particularly preferred compositions comprising whey protein isolate, including the composition known as Immunocal®. This exemplary whey protein isolate composition as described in CA 2,142,277 may be characterized by having a solubility index of about 99.5% at pH 4.6; about 58% βL (beta-lactoglobulin) protein composition, about 11% αL (alpha-lactalbumin) protein composition, about 10% serum albumin (i.e. BSA) protein composition, and about 22% immunoglobulin (i.e. Ig) protein composition. A process for preparing such a composition is also described in detail in CA 2,142,277. Immunocal® (Natural Product Number (NPN) 80004370 issued with Health Canada) is now a commercially available whey protein isolate composition available from Immunotec®.

Further description of whey protein isolates and concentrates may be found in Example 2 below.

In an embodiment, compositions as described herein may be administered orally. For example, compositions as described herein may be reconstituted in, or may comprise, a liquid carrier (for example, water or juice), allowing for straightforward oral administration. The person of skill in the art having regard to the teachings herein will be able to select a suitable administration to suit a particular subject and/or particular therapeutic application.

In certain non-limiting embodiments, it is contemplated that compositions as described herein may be administered orally in an amount suitable for achieving a desired effect. In certain non-limiting embodiments, compositions as described herein may be administered orally in a dosage of about 20-40 grams per day, for example, and may be administered once or more than once daily, for example.

It will be understood that compositions as described herein may be administered as part of a treatment regimen including other drugs, pharmaceutical compositions, or therapies used in the treatment of autism. Compositions as described herein may be for administration simultaneously, sequentially, in combination with, or separately from such other drugs, pharmaceutical compositions, or therapies.

As will be understood, compositions comprising whey protein isolate and/or whey protein concentrate as described herein may serve as a glutathione precursor by providing an enriched source of bioavailable cysteine following administration.

All references cited herein are hereby incorporated by reference in their entirety.

It will be appreciated that embodiments and examples are provided herein for illustrative purposes intended for those skilled in the art, and are not meant to be limiting in any way. One or more illustrative embodiments have been described by way of example. It will be understood to persons skilled in the art that a number of variations and modifications can be made without departing from the scope of the invention as defined in the claims.

EXAMPLE 1

Effects of a Cysteine-Rich Whey Protein Isolate (Immunocal®) on Core Areas of Autism Behaviour and Antioxidant Capacity: A Randomized, Double Blind Controlled Study A double-blind placebo-controlled study was used to evaluate the effectiveness of a cysteine-rich whey protein, known to raise glutathione levels, on autism behaviors in children ages 3-5. Several behavioral tests (a total of 8 validated behavioural tests) were used in order to assess different areas of behavior. This study further investigated the correlation between improvements in behaviors and changes in GSH levels.

In this study, the subjects in the intervention, whey protein supplement group, and in the control group were children. In the control group, a rice protein powder, which mimics the amount of protein obtained from whey, was used as placebo.

In this study, as described in detail hereinbelow, both the placebo (n=19) and the intervention (n=21) groups demonstrated improvements from baseline to follow-up in some areas of autism behavior. However, when comparing the changes between the two groups, the one assigned to the intervention, supplement demonstrated significant improvements in various scores of the parent-rated Vineland Adaptive Behavior Scales: adaptive behavior (p=0.03), socialization (p=0.03), maladaptive behavior (p=0.04) and internalizing (p=0.02). Significant increases in glutathione levels were observed in the intervention group when compared to changes in the placebo group (p=0.04). Surprisingly, individual improvements in the intervention arm did not correlate with increases in glutathione levels (p=0.50). A group of responders were identified within the intervention group (60%). The responders' average age was about 4.28, indicating that these children were older (by about 9.0 months, p=0.03) than non-responders, and had higher baseline levels of GSH compared to the non-responders (127.8±19.8 versus 51.3±9.87 nM/$10^5$ WBC, p=0.01). The incidence of adverse reactions was similar in both intervention and placebo groups. Based on results of this study, cysteine-rich whey protein supplementation may provide a safe and effective treatment for improving one or more core areas of autism behaviors, while optionally also increasing GSH levels.

Methods

This study was approved by the International Review Board at Nova Southeastern University in Fort Lauderdale, Fla., USA, with clinicaltrials.gov trial identifier number NCT01366859.

Study Population

Participants were recruited from South Florida by Mailman Segal Center, by use of snowball sampling. Parents' self-reported ASD diagnosis but was confirmed after inclusion in the study according to the Diagnostic Statistical Manual (DSM-IV and DSM-V) by clinical psychologists using the ADOS test at baseline. Inclusion criteria included that participants have ASD, and be within 3-5 years of age at the start and during the trial period.

Exclusion criteria included: (i) allergies to milk, rice or nuts; (ii) major medical problems, including cardiac, liver, endocrine or renal disease; (iii) history of seizure disorder or gross neurological deficit; (iv) concomitant treatment with psychiatric medication; (v) current diet supplementation with N-acetylcysteine, alpha lipoic acid, whey protein or higher than regular multivitamin doses of vitamin B12 or folic acid; (vi) comorbid diagnosis: Fragile X syndrome, tuberous sclerosis, phenylketonuria or fetal alcohol syndrome or (vii) acute illness. The comorbid conditions of Fragile X syndrome, tuberous sclerosis, phenylketonuria or fetal alcohol syndrome were excluded because these children present some autistic behavioral features, but the origin is known. Genetic tests were not performed by the by investigators to confirm exclusion diagnostics, however, the children's pediatricians confirmed exclusion and inclusion criteria. Subjects in both groups were able to continue taking multi-vitamins, probiotics and other medications/supplements as long as they were not mentioned as exclusion criteria (known to significantly raise glutathione levels).

Study Visits

Visit 1 (Mailman Segal Center) consisted of initial assessment of inclusion and exclusion criteria. A detailed medical history, current dug/supplement intake and some demographic information about the child and parents, was collected.

Visit 2 appointment consisted of a wellness exam conducted by Nova Southeastern University pediatricians to confirm that the child was otherwise healthy. A blood sample was obtained at this visit to assess oxidative stress biomarkers. Separate samples were collected to assess liver and kidney function as well as cell blood count.

Visits 3 and 4 for baseline measurements consisted of all behavioral assessments conducted by Nova Southeastern University clinical psychologists. These consecutive visits were conducted no later than 15 days after visit 2. All eight (8) behavioral assessments (see below) were split between these two visits lasted an average of two hours. When needed, a third appointment was scheduled to avoid overwhelming the child with excessive testing and to minimize evaluation errors. These two visits were scheduled within a 15-day window. At the end of this visit, children were randomized to either placebo (rice protein) or intervention (CRWP; (Immunocal®, Immunotec Inc.)) and parents were given a diary to measure adverse effects and/or unusual events together with the canister containing the study product in powder form with measuring scoop.

Visit 5 was scheduled between weeks 6 and 7 (middle visit) only to collect the remaining powder in the canister, parents' diaries, and provided new canister for next period. The main purpose of this visit was to assess compliance and record adverse events.

Visits 6 and 7 for follow-up assessment at week 12 were conducted as indicated for baseline visits 3 and 4. The same clinical psychologists performed the behavioral tests in the same sequence as baseline. Parents were instructed to continue with the study product daily dose until the next and final visit 8.

Visit 8 follow-up/final visit was scheduled no later than 7 days after visit 7 (weeks 12-13). Visit 8 was performed as stated previously for visit 2. The final canister and parents' diaries were collected at this time.

The trial period was 90-days.

Intervention and Placebo

The intervention group received cysteine-rich whey protein isolate (CRWP), commercially available as Immunocal®, which was provided by Immunotec Inc. (Montreal, Quebec, Canada). It should be noted that Immunocal® is included in the Physician's Desk Reference ("Immunocal," 2013). Rice protein was used as placebo to mimic the protein load in the intervention group and was obtained from Thera-Plantes Inc., (Montreal, Quebec, Canada). Both CRWP (Immunocal®) and placebo (rice protein) treatments were provided to parents and caregivers in powder form in canisters. A daily dose of 0.5 grams/kg for children under 20 kg or a 10-gram dose for those over 20 kg was taken by children in both arms of the study for at least 90 days. Clear instructions were given to parents and caregivers on how to reconstitute the powders using liquids and/or foods avoiding the use of a blender or heat. Parents were told how to measure the dose using measuring spoons provided by study personnel. Half of the dose (with some excess) was given in a canister at visit 4 after randomization. The remaining half was provided at visit 5 (middle visit). Parents were asked to return the canisters to the study personnel for compliance assessment.

Outcome Measures

All primary (behavioral measurements) and secondary outcomes (intracellular glutathione levels and adverse events) were obtained at baseline and study end. Diaries given to parents at visits 4 and 5 and designed to collect any side effect and/or unusual events, were also requested after participant completed study. All study staff, participants, and parents/legal guardians were blind to treatment allocation.

Primary Outcomes

Behavioral analysis in areas of autism behavior and severity, communication, developmental status and behavioral problems were conducted at baseline visits 3 and 4 as well as at the end of the study during follow-up visits 6 and 7. Trained assessors administered the battery of assessments, 8 different tests in total, over a consecutive two-day period. Assessors achieved reliability with each other before beginning the assessment process and to minimize sources of error, the same assessor was responsible for administering the entire battery for a participant (baseline and follow-up). Additionally, the behavioral assessment teams were blind to each other's results.

Three behavioral assessments were performed in the autism behaviors and severity domain: 1) Autism Diagnostic Observation Schedule (ADOS), 2) Childhood Autism Rating Scale (CARS) and 3) the Autism Diagnostic Interview-Revised (ADI-R). The ADOS and the ADI-R were utilized solely as inclusion criteria measurements. The ADOS is a semi-structured assessment that consists of various activities that allow the observation of social and communication behaviors related to the diagnosis of ASD (Lord et al. 1989). In this study, participants either were given Module 1 or 2. Module 1 is intended for those who do not consistently use phrase speech while Module 2 is used for those who show phrase speech but are not verbally fluent. The CARS is a 15-item behavior rating scale used to identify children with autism and to distinguish the severity of the disorder (Schopler, Reichler, DeVellis, and Daly 1980). The ADI-R is a comprehensive interview administered to parents that provides a thorough assessment of individuals with ASD (Lord, Le Couteur, and Rutter 1994). It focuses on three functional domains: Language/Communication; Reciprocal Social Interactions, and Restricted/Repetitive and Stereotyped Behaviors and Interests.

Verbal communication was assessed by the Pre-school Language Scale-Fifth edition (PLS-5) and the Social Communication Questionnaire (SCQ). In preschoolers with ASD, the PLS-5 can be used to obtain a general index of early syntax and sematic skill (Volden et al. 2011). The SCQ is a brief instrument that evaluates communication skills and social functioning in children with ASD (Rutter and Lord 2003). It is completed by the child's primary caregiver.

The developmental status of each participant was measured by the Mullen Scales of Early Learning (MSEL) and the Vineland Adaptive Behavior Scale, 2nd edition (VABS-II). The MSEL is a developmentally integrated system that assesses language, motor and perceptual abilities for children ages birth to 68 months of age (Mullen 1995). It contains five scales: Gross Motor, Visual Reception, Fine Motor, Expressive Language and Receptive Language. This assessment identified a child's strengths and weaknesses and assesses early intellectual development and readiness for school. The VABS-II is completed by the child's primary caregiver and is an individually administered measure of adaptive behavior, especially in those with developmental disorders (Manohari, Raman, and Ashok 2013; Sparrow, Balla, and Cicchetti 1984). It can be given from birth to adulthood and is comprised of the following domains: Communication (Receptive, Expressive, Written); Daily Living Skills (Personal, Domestic, Community); Socialization (Interpersonal Relationships, Play and Leisure Time, Coping Skills); Motor Skills (Fine, Gross); and an optional Maladaptive Behavior Index (Internalizing, Externalizing and Other). The VABS-II is utilized to assess personal and social sufficiency with these four major domains.

Behavioral issues were measured by the Child Behavior Checklist 1½-5 LDS (CBCL). The CBCL is an instrument used to rate a child's problem behaviors and competencies (Achenbach 1991; Achenbach and Rescorla 2000) it was completed by the child's caregiver.

Glutathione Measurements

Intracellular glutathione levels and markers of oxidative stress were taken in blood cells from treatment and control samples collected during weeks 0 (baseline) and week 12 (follow-up). A trained pediatric phlebotomist conducted all blood draw procedures. Blood samples were collected by venipuncture in BD Vacutainer® CPT™ Mononuclear Cell Preparation Tubes, with sodium heparin, immediately placed in ice water and then centrifuged at 2,000 g at 4° C. for 10 minutes. The amounts of total, reduced and oxidized glutathione were quantified using the Tietze method (Tietze 1969). Standards containing the reduced form of glutathione (GSH) or the oxidized form of glutathione (GSSG) from 20 to 0.015 uM in 2.5% sulfosalicyclic acid were used as standards for GSH and GSSG calibration curves. The difference in absorbance recorded at 412 nm before and 6 minutes after the addition of NADPH in the presence of glutathione reductase was utilized to calculate the amount of total glutathione. GSSG was quantified in the presence of vinylpyridine and triethanolamine using the same procedure. Reduced glutathione was calculated by subtracting the GSSG concentration from the total glutathione content.

Secondary Outcomes

Any adverse event during the course of the study was monitored and reported to the study staff at week 6 (visit 5) or week 12 (visit 8) in the clinic or directly to principle investigator throughout the study. Adverse events were considered related to the treatment if they started or worsened following the start of the trial. If they were persistent or severe, the parents were offered the option to discontinue the study.

Additionally, liver and kidney function as well as a cell blood count were assessed in blood and urine at weeks 0 and week 12. The comprehensive metabolic profile was reviewed by physicians and compared to known reference ranges.

The child's guardian was given the CRWP or the placebo as randomized in powder form in canisters at two different visits, at week 0 (baseline) and week 6, and asked to bring the used canisters back to study personnel after weeks 6 and 12 (follow-up) for it to be weighed. The weight of the canister and the parent's diary form were taken into consideration for compliance assessment.

Statistical Analysis

An intent-to-treat approach was used during the statistical analysis of this study. Descriptive statistics were calculated for all study variables. This included means and standard deviations for continuous data, counts and percentages for categorical measures. We assessed the differences in demographic measures between the two groups at baseline using chi-square tests.

To look for differences between the CRWP and Placebo groups for the physiological assessments a series of mixed, generalized linear models were conducted. All models included subjects' gender, age, mother's age, father's age and race as covariates. Post-hoc tests were conducted using a Bonferroni adjustment. To look for differences between the CRWP and placebo groups for the psychological measurements, a series of paired and unpaired t-tests were conducted using a Bonferroni adjustment. Cohen's D was used to determine the effect size between the two groups. RStudio and R 3.2.2 was used for all statistical analysis, and significance was accepted at p<0.05.

Results

Figure 3:
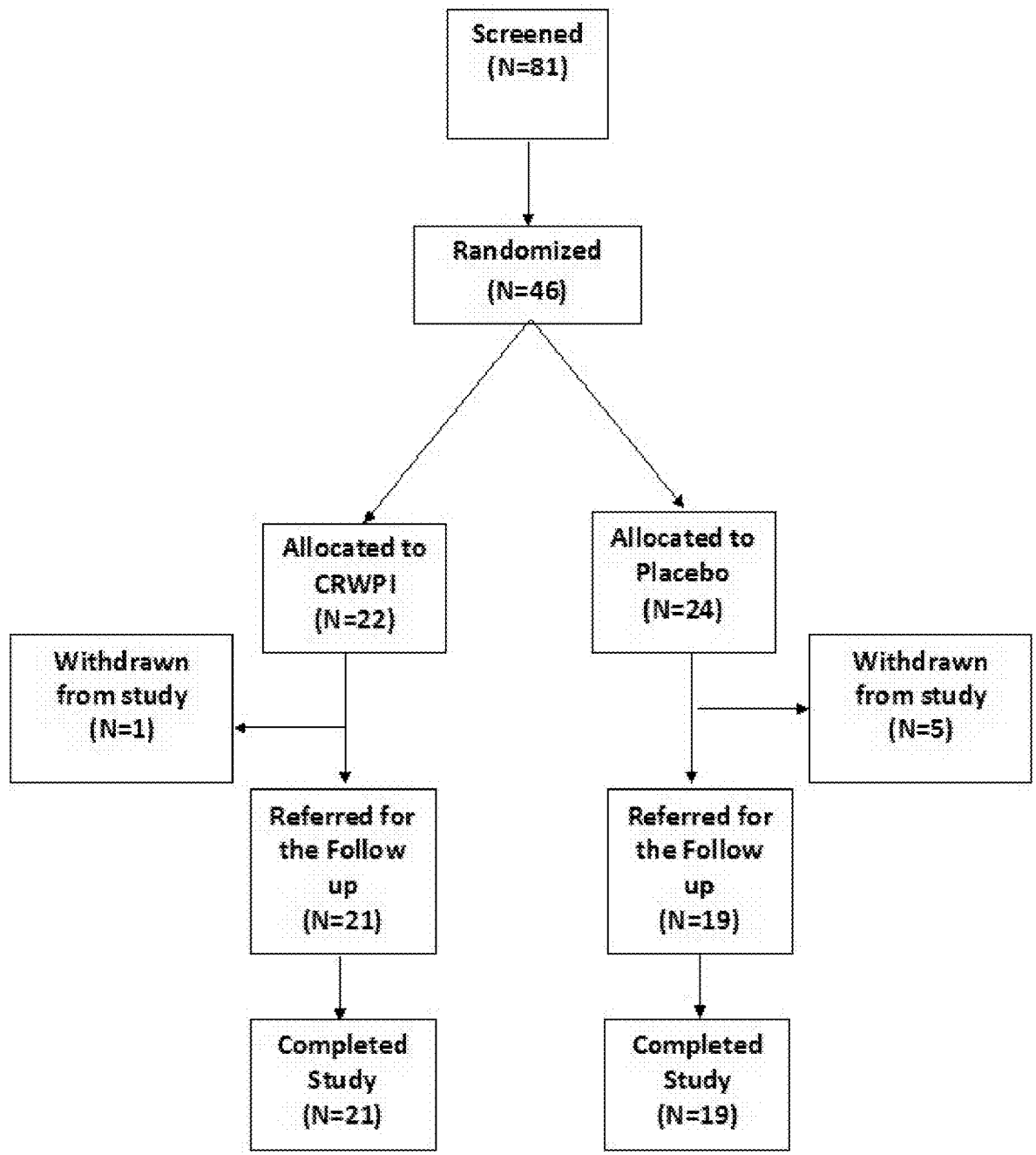
FIG. 3 shows a Flow Diagram showing distribution of subjects at each stage of the study described in Example 1.

A total of 81 participants were screened in this study; 46 were randomized (CRWP: 21 and 24 to placebo). A total of 40 participants completed the 90-days/3-month treatment period (CRWP: 21 and 19 to placebo). (FIG. 3).

At baseline, subject demographic characteristics were similar across both groups (Table 1). The average age of subjects in both groups was (placebo=3.9±0.73 and CRWP=3.9±0.77) years of age. The majority of subjects were male (placebo=83% and CRWP=90%). A wide variety of races were represented in the study, which is indicative of the diversity within the South Florida community. Parental demographic information was also similar across groups, with no significant difference in parents' age between groups. However, the percentage of women who only graduated from high school was significantly different in the placebo group in comparison to the CRWP group (p=0.04). There were also no differences between the groups at baseline in terms of diagnostic criteria, or scores in the ADI-R and ADOS assessments (Table 1). Finally, there were no significant differences in medications/supplements taken by the placebo or CRWP groups.

TABLE 1

Demographic Information for Placebo and Intervention Groups Taken at Baseline

| | Placebo (n = 24) | Intervention (n = 21) | p-value |
|---|---|---|---|
| Subject Information: | | | |
| Age (years) | 3.9 | 3.9 | 0.72 |
| Males, N (%) | 20 (83) | 19 (90) | 0.48 |
| Ethnicity, N (%) | | | |
| Hispanic | 5 (21) | 10 (48) | 0.11 |
| Not Hispanic or Latino | 6 (25) | 3 (14) | 0.37 |
| Race, N (%) | | | |
| Asian | 0 (0) | 1 (5) | 0.28 |
| Native Hawaiian or other Pacific Islander | 1 (4) | 0 (0) | 0.34 |
| Black or African American | 7 (29) | 3 (14) | 0.23 |
| White | 11 (46) | 12 (57) | 0.45 |
| Other | 0 (0) | 2 (10) | 0.12 |
| Paternal Information | | | |
| Paternal Age at birth (years) | 35.9 | 36.2 | 0.77 |
| High school graduate, N (%) | 3 (14) | 6 (32) | 0.18 |
| Some college/Technical, N (%) | 4 (19) | 5 (26) | 0.55 |
| College/Professional, N (%) | 14 (67) | 8 (42) | 0.18 |
| Maternal Information | | | |
| Maternal Age at birth (years) | 34.1 | 34.8 | 0.77 |
| High school graduate, N (%) | 4 (17) | 0 (0) | 0.04* |
| Some college/Technical, N (%) | 3 (13) | 4 (20) | 0.55 |
| College/Professional, N (%) | 17 (70) | 16 (80) | 0.69 |
| Diagnostic Characteristics: | | | |
| Autism Diagnostic Interview Revised | | | |
| ADI-R (Reciprocal Social Interaction) | 12.9 ± 1.54 | 11.7 ± 1.47 | 0.41 |
| ADI-R (Verbal) | 9.11 ± 1.02 | 10.2 ± 1.31 | 0.22 |
| ADI-R (Non-verbal) | 8.40 ± 1.12 | 9.58 ± 1.16 | 0.42 |
| ADI-R (Restricted Behavior) | 6.05 ± 0.55 | 5.26 ± 0.49 | 0.80 |
| Total | 29.0 ± 1.71 | 26.11 ± 2.19 | 0.24 |
| Autism Diagnostic Observation | | | |
| Composite Score Module 1: | 13.5 ± 1.10 | 14.3 ± 1.92 | 0.73 |
| ADOS Communication Score | 5.07 ± 0.62 | 6.00 ± 0.80 | 0.23 |
| ADOS Social Interaction Score | 8.47 ± 0.83 | 8.25 ± 1.35 | 0.66 |
| ADOS Play Score | 2.73 ± 0.42 | 2.58 ± 0.43 | 0.61 |
| ADOS Stereotyped Behaviors and Restricted Interests Total Score | 2.47 ± 0.51 | 2.92 ± 0.68 | 0.41 |
| Composite Score Module 2: | 10.7 ± 1.66 | 11.2 ± 1.85 | 0.85 |
| ADOS Communication Score | 4.33 ± 0.83 | 4.78 ± 0.92 | 0.69 |
| ADOS Social Interaction Score | 6.33 ± 1.01 | 6.44 ± 1.08 | 0.24 |
| ADOS Play Score | 1.11 ± 0.31 | 0.89 ± 0.45 | 0.66 |
| ADOS Stereotyped Behaviors and Restricted Interests Total Score | 2.11 ± 0.35 | 1.67 ± 0.47 | 0.60 |

Behavioral assessments at baseline were successfully performed in 24 subjects within placebo the group and 20 subjects within the CRWP group (Table 2). In general, average scores across groups were similar for the majority of behavioral assessments; however, some differences were noted. In the VABS-II, the placebo group had a significantly higher score in daily living skills domain (p=0.04), coping skills (p=0.02), motor skills domain (p=0.04) and fine motor skills (p=0.03) in comparison to the CRWP group. Higher scores in the VABS-II equates to more adaptive behaviors suggesting the placebo group was less affected. In the Child Behavior Checklist, the CRWP group had higher scores in stress problems T-score (p=0.04).

TABLE 2

Changes in Behavioural Assessments in Placebo and CRWP Group from Baseline to Follow-up.

| Behavior Assessments: | Placebo | | | | CRWP | | | | Baseline placebo vs. Baseline intervention p-value | p-value of Δ vs. Δ |
|---|---|---|---|---|---|---|---|---|---|---|
| | Baseline (n = 24) | 12 weeks (n = 21) | Δ | p-value | Baseline (n = 21) | 12 weeks (n = 19) | Δ | p-value | | |
| Childhood Autism Rating Scale | | | | | | | | | | |
| CARS Behavior T-score | 40.0 ± 1.87 | 37.4 ± 1.89 | −2.61 | 0.02* | 40.2 ± 2.58 | 38.4 ± 2.83 | −1.80 | 0.04* | 0.95 | 0.47 |
| Preschool Language Scales | | | | | | | | | | |
| Total Language Score | 67.3 ± 3.39 | 66.71 ± 3.68 | −0.54 | 0.46 | 73.38 ± 4.48 | 68.80 ± 5.67 | −4.58 | 0.30 | 0.27 | 0.17 |
| Standard Score | 139 ± 6.28 | 130.30 ± 7.70 | −8.70 | 0.17 | 149.00 ± 8.59 | 145.40 ± 9.65 | −3.60 | 0.89 | 0.35 | 0.84 |
| Auditory Comprehension | 66.9 ± 3.59 | 68.33 ± 4.15 | 1.45 | 0.47 | 75.76 ± 4.51 | 74.95 ± 5.01 | −0.81 | −0.77 | 0.23 | 0.93 |
| Expressive Communication | 69.7 ± 3.12 | 68.76 ± 3.16 | −0.95 | 0.46 | 73.10 ± 4.28 | 71.63 ± 4.72 | −1.47 | 0.91 | 0.52 | 0.46 |
| Social Communication Questionnaire | 16.4 ± 1.17 | 14.4 ± 1.43 | −1.99 | 0.02* | 16.57 ± 1.12 | 14.4 ± 1.04 | −2.22 | 0.04† | 0.41 | 0.88 |
| Mullen Scales of Early Learning T score | | | | | | | | | | |
| Early Learning Composite Score | 61.0 ± 2.82 | 63.3 ± 3.84 | 2.33 | 0.12 | 67.1 ± 3.95 | 68.6 ± 4.53 | 1.55 | 0.44 | 0.20 | 0.20 |
| Visual Reception | 30.8 ± 2.67 | 33.1 ± 3.49 | 2.34 | 0.21 | 35.1 ± 2.49 | 35.0 ± 3.30 | −0.05 | 0.69 | 0.25 | 0.15 |
| Fine Motor | 27.3 ± 2.12 | 28.7 ± 2.80 | 1.47 | 0.31 | 32.4 ± 3.13 | 33.2 ± 4.10 | 0.81 | 0.62 | 0.35 | 0.45 |
| Receptive Language | 25.3 ± 1.57 | 28.3 ± 2.50 | 2.91 | 0.08 | 28.4 ± 2.41 | 28.2 ± 2.69 | −0.28 | 0.97 | 0.27 | 0.63 |
| Vineland Adaptive Behavior Scales | | | | | | | | | | |
| Adaptive Behavior Composite Score | 82.8 ± 3.41 | 82.9 ± 3.97 | 0.13 | 0.47 | 71.5 ± 2.85 | 74.4 ± 3.47 | 2.85 | 0.05† | 0.08 | 0.03† |
| Communication Domain | 79.9 ± 3.56 | 79.76 ± 4.41 | −0.16 | 0.45 | 75.1 ± 4.47 | 77.2 ± 5.02 | 2.07 | 0.05* | 0.40 | 0.15 |
| Receptive | 10.3 ± 0.66 | 10.81 ± 0.98 | 0.56 | 0.31 | 9.43 ± 0.80 | 9.63 ± 0.84 | 0.20 | 0.23 | 0.43 | 0.84 |
| Expressive | 9.38 ± 0.67 | 9.905 ± 0.69 | 0.53 | 0.17 | 9.38 ± 0.81 | 9.95 ± 1.09 | 0.57 | 0.05* | 0.87 | 0.57 |
| Written | 15.5 ± 0.86 | 15.2 ± 0.87 | −0.27 | 0.28 | 14.48 ± 0.87 | 14.39 ± 0.80 | −0.09 | 0.17 | 0.43 | 0.24 |
| Daily Living Skills Domain | 82.9 ± 3.42 | 83.0 ± 3.42 | 0.12 | 0.24 | 74.52 ± 2.99 | 74.84 ± 3.39 | −0.32 | 0.26 | 0.04* | 0.25 |
| Personal | 11.4 ± 0.76 | 11.5 ± 0.83 | 0.10 | 0.45 | 9.95 ± 0.55 | 11.00 ± 0.79 | 1.05 | 0.03† | 0.22 | 0.05* |
| Domestic | 13.5 ± 0.63 | 13.7 ± 0.56 | 0.21 | 0.47 | 12.10 ± 0.54 | 11.42 ± 0.50 | −0.68 | 0.37 | 0.11 | 0.74 |
| Community | 12.2 ± 0.64 | 12.3 ± 0.69 | 0.16 | 0.46 | 10.95 ± 0.54 | 10.68 ± 0.59 | −0.27 | 0.74 | 0.16 | 0.64 |
| Socialization Domain | 79.1 ± 2.30 | 78.7 ± 3.2 | −0.32 | 0.35 | 71.24 ± 2.84 | 73.89 ± 3.69 | 2.65 | 0.04* | 0.06 | 0.04* |
| Interpersonal | 10.4 ± 0.57 | 10.2 ± 0.79 | −0.23 | 0.26 | 9.33 ± 0.60 | 9.632 ± 0.78 | 0.30 | 0.27 | 0.20 | 0.14 |
| Play and Leisure Time | 10.5 ± 0.58 | 10.4 ± 0.55 | −0.12 | 0.20 | 9.33 ± 0.61 | 9.579 ± 0.70 | 0.25 | 0.33 | 0.20 | 0.28 |
| Coping Skills | 13.1 ± 0.47 | 13.4 ± 0.74 | 0.27 | 0.46 | 11.20 ± 0.50 | 11.95 ± 0.67 | 0.75 | 0.04* | 0.02* | 0.23 |
| Motor Skills Domain | 86.4 ± 3.33 | 87.0 ± 4.27 | 0.57 | 0.61 | 78.62 ± 2.85 | 77.68 ± 2.89 | −0.94 | 0.74 | 0.04* | 0.59 |
| Gross | 12.7 ± 0.69 | 12.5 ± 0.84 | −0.19 | 0.83 | 11.81 ± 0.51 | 11.16 ± 0.44 | −0.65 | 0.34 | 0.34 | 0.88 |
| Fine | 12.8 ± 0.63 | 13.2 ± 0.75 | 0.35 | 0.16 | 11.10 ± 0.61 | 11.47 ± 0.64 | 0.37 | 0.03* | 0.03* | 0.63 |
| Maladaptive Behavior Domain | 19.2 ± 0.52 | 19.2 ± 0.55 | −0.05 | 0.47 | 20.05 ± 0.50 | 19.44 ± 0.56 | −0.61 | 0.16 | 0.26 | 0.04* |
| Internalizing | 19.3 ± 0.56 | 19.5 ± 0.60 | 0.16 | 0.17 | 20.20 ± 0.43 | 19.53 ± 0.69 | −0.67 | 0.12 | 0.29 | 0.02* |
| Externalizing | 16.9 ± 0.66 | 17.0 ± 0.73 | 0.05 | 0.99 | 18.05 ± 0.59 | 17.58 ± 0.39 | −0.47 | 0.40 | 0.21 | 0.48 |

TABLE 2-continued

Changes in Behavioural Assessments in Placebo and CRWP Group from Baseline to Follow-up.

| Behavior Assessments: | Placebo | | | | CRWP | | | | Baseline placebo vs. Baseline intervention p-value | p-value of Δ vs. Δ |
|---|---|---|---|---|---|---|---|---|---|---|
| | Baseline (n = 24) | 12 weeks (n = 21) | Δ | p-value | Baseline (n = 21) | 12 weeks (n = 19) | Δ | p-value | | |
| Child Behavior Checklist | | | | | | | | | | |
| Total Problems | 61.8 ± 2.20 | 60.3 ± 2.40 | −1.50 | 0.02* | 62.60 ± 2.00 | 59.00 ± 2.24 | −3.60 | 0.30 | 0.82 | 0.52 |
| Emotionally Reactive T-Score | 61.0 ± 2.08 | 60.3 ± 1.78 | −0.71 | 0.61 | 62.79 ± 2.07 | 58.28 ± 1.92 | −4.51 | 0.04* | 0.55 | 0.31 |
| Anxious/Depressed T-score | 55.9 ± 1.30 | 56.2 ± 1.72 | 0.28 | 0.95 | 58.00 ± 1.74 | 54.94 ± 1.51 | −3.06 | 0.11 | 0.46 | 0.21 |
| Somatic Complaints T-score | 58.7 ± 1.68 | 57.2 ± 1.77 | −1.46 | 0.12 | 58.0 ± 0.54 | 56.3 ± 1.81 | −1.67 | 0.35 | 0.65 | 0.70 |
| Withdrawn T-score | 69.2 ± 1.85 | 67.3 ± 2.51 | −1.88 | 0.04† | 69.0 ± 1.82 | 66.1 ± 2.28 | −2.89 | 0.51 | 0.93 | 0.54 |
| Sleep Problems T-score | 58.1 ± 2.24 | 56.6 ± 1.88 | −1.46 | 0.49 | 59.9 ± 2.25 | 59.2 ± 1.84 | −0.67 | 0.43 | 0.42 | 0.21 |
| Attention Problems T-score | 62.2 ± 1.50 | 62.8 ± 2.12 | 0.59 | 0.55 | 62.2 ± 1.95 | 62.2 ± 1.71 | −0.04 | 0.79 | 0.86 | 0.63 |
| Aggressive Behavior T-score | 59.5 ± 2.61 | 57.7 ± 1.91 | −2.31 | 0.04* | 57.7 ± 1.96 | 56.4 ± 1.81 | −1.29 | 0.22 | 0.98 | 0.80 |
| DSM Oriented Scale Scores: | | | | | | | | | | |
| Affective Problems T-score | 59.6 ± 1.91 | 58.6 ± 2.01 | −0.99 | 0.27 | 62.1 ± 2.18 | 59.3 ± 2.18 | −2.72 | 0.62 | 0.86 | 0.78 |
| Anxiety Problems T-score | 57.3 ± 1.37 | 55.6 ± 1.48 | −1.64 | 0.47 | 59.3 ± 2.18 | 57.9 ± 2.04 | −1.64 | 0.42 | 0.64 | 0.82 |
| Pervasive Developmental Problems T-score | 70.4 ± 1.63 | 69.7 ± 2.15 | −0.72 | 0.24 | 70.6 ± 1.83 | 66.8 ± 2.19 | −3.80 | 0.21 | 0.95 | 0.78 |
| Attention Deficit/Hyperactivity T-score | 58.9 ± 1.42 | 57.9 ± 1.49 | −1.05 | 0.17 | 58.1 ± 1.56 | 57.2 ± 1.46 | −0.88 | 0.42 | 0.58 | 0.98 |
| Oppositional Defiant T-score | 57.9 ± 1.97 | 57.3 ± 1.67 | −0.54 | 0.11 | 56.8 ± 2.19 | 56.3 ± 1.80 | −0.51 | 0.99 | 0.98 | 0.50 |
| Total Scares: | | | | | | | | | | |
| Internalizing Problems T-score | 62.4 ± 1.84 | 60.3 ± 2.17 | −2.06 | 0.04* | 63.00 ± 1.98 | 59.40 ± 2.05 | −3.60 | 0.13 | 0.82 | 0.95 |
| Externalizing Problems T-score | 58.8 ± 2.44 | 57.8 ± 2.24 | −1.02 | 0.16 | 58.4 ± 1.92 | 56.4 ± 1.83 | −1.97 | 0.21 | 0.90 | 0.91 |
| Stress problems T-score | 61.8 ± 2.01 | 62.3 ± 1.78 | 0.42 | 0.41 | 63.6 ± 2.68 | 61.7 ± 3.33 | −1.90 | 0.65 | 0.04* | 0.38 |

*p-value < 0.05 using two tail t-test;
†p-value < 0.05 using one tail t-test.

Additionally, at baseline, the amount of total glutathione, oxidized glutathione, reduced glutathione and the ratio of oxidized to reduced glutathione was measured in each subjects' leukocytes. Table 3 shows these baseline measurements for 24 subjects in the placebo group and 20 subjects in the CRWP group. There were no significant differences in any of the glutathione measurements taken at baseline between both groups (Table 3).

Primary Outcomes

When comparing baseline to follow-up changes in the CRWP and placebo groups, behavioral improvements were seen in both groups as shown in Table 2 (p-values in the placebo and CRWP columns), however the CRWP group improved in more areas than the placebo group. In the areas of autism behaviors and severity, there were no significant differences between baseline and after intervention in the ADOS for both Placebo and CRWP groups. In the ADI-R,

TABLE 3

Change in Glutathione Levels from Baseline to Follow-up in Placebo and Intervention Groups

| Glutathione Levels: (nM/10*5 WBC) | Placebo (Mean ± SEM) | | | | Intervention (Mean ± SEM) | | | | Baseline placebo vs. baseline intervention | p-value of Δ vs. Δ |
|---|---|---|---|---|---|---|---|---|---|---|
| | Baseline (n = 24) | 12 weeks (n = 16) | Δ | p-value | Baseline (n = 20) | 12 weeks (n = 20) | Δ | p-value | | |
| tGSH | 104.2 ± 15.8 | 88.0 ± 12.79 | −16.22 | 0.50 | 113.1 ± 16.1 | 166.7 ± 37.2 | 3.60 | 0.17 | 0.77 | 0.02* |
| GSSG | 10.9 ± 1.57 | 8.99 ± 1.36 | −1.86 | 0.78 | 7.95 ± 1.34 | 12.88 ± 2.70 | 4.93 | 0.22 | 0.14 | 0.12 |
| GSH | 82.5 ± 13.9 | 66.3 ± 9.8 | −16.16 | 0.53 | 97.2 ± 15.0 | 136.0 ± 34.4 | 38.8 | 0.47 | 0.13 | 0.04* | the CRWP group improved significantly in the reciprocal social interaction domain (p=0.04). Both groups significantly improved in the total ADI-R score (Placebo p=0.04, CRWP p=0.05). In the CARS assessment for autistic behaviors, those in the CRWP group improved in the behavior t-score (p=0.04) but so did those in the placebo group (p=0.02). In the communication assessments, there were no significant changes in the PLS in either group. However, there were improvements in the SCQ in both the CRWP (p=0.04) and the placebo group (p=0.02). The intervention group also demonstrated improvements in the emotionally reactive portion of the CBCL (p=0.04), while the placebo group had a decrease in total problems (p=0.02), aggressive behavior (p=0.04) and a worsening of internalizing problems (p=0.04). When assessing adaptive behaviour, the most significant improvements were made in the VABS-II (Table 2). The CRWP group showed significant improvements from baseline to follow-up in the adaptive behavior composite score (p=0.05), communication domain (p=0.05), socialization domain (p=0.04,) and daily living skills domain (p=0.03). They also had significant improvements from baseline to follow-up in multiple sub-domains such as expressive communication (p=0.05), personal daily living skills (p=0.03), coping skills (p=0.04) and fine motor skills (p=0.03). The placebo group did not show any changes in their developmental status as per VABS-II. Table 2 also shows improvements made in both groups within the: CARS, SCQ and CBCL.

After the 3-month intervention, the parent-rated VABS-II was the instrument that showed statistically significant improvement in the CRWP when compared to changes in the placebo group (effect size 0.98; 95% confidence interval (CI) 1.42 to 4.02; p=0.031) with medium-large effect size. Thus, there was a significant improvement in the VABS-II composite score as well as important changes in multiple domains/sub-domains representing different aspects of autism symptoms in the intervention group. Specifically, the socialization domain (effect size 1.07; 95% CI 1.82 to 4.28; p=0.04), domestic daily living skills (effect size 0.73; 95% CI 0.34 to 1.55; p=0.05), maladaptive behavior domain (effect size 0.54; 95% CI −1.12 to 0.10; p=0.04) and internalizing subdomain (effect size 0.73; 95% CI −1.40 to 0.34; p=0.02) all showed significant improvements. When using a similar analysis, no significant changes were observed in other assessments conducted in this study (ADOS, ADI-R, CARS, CBCL, PLS, SCQ and MSEL).

Figure 4:
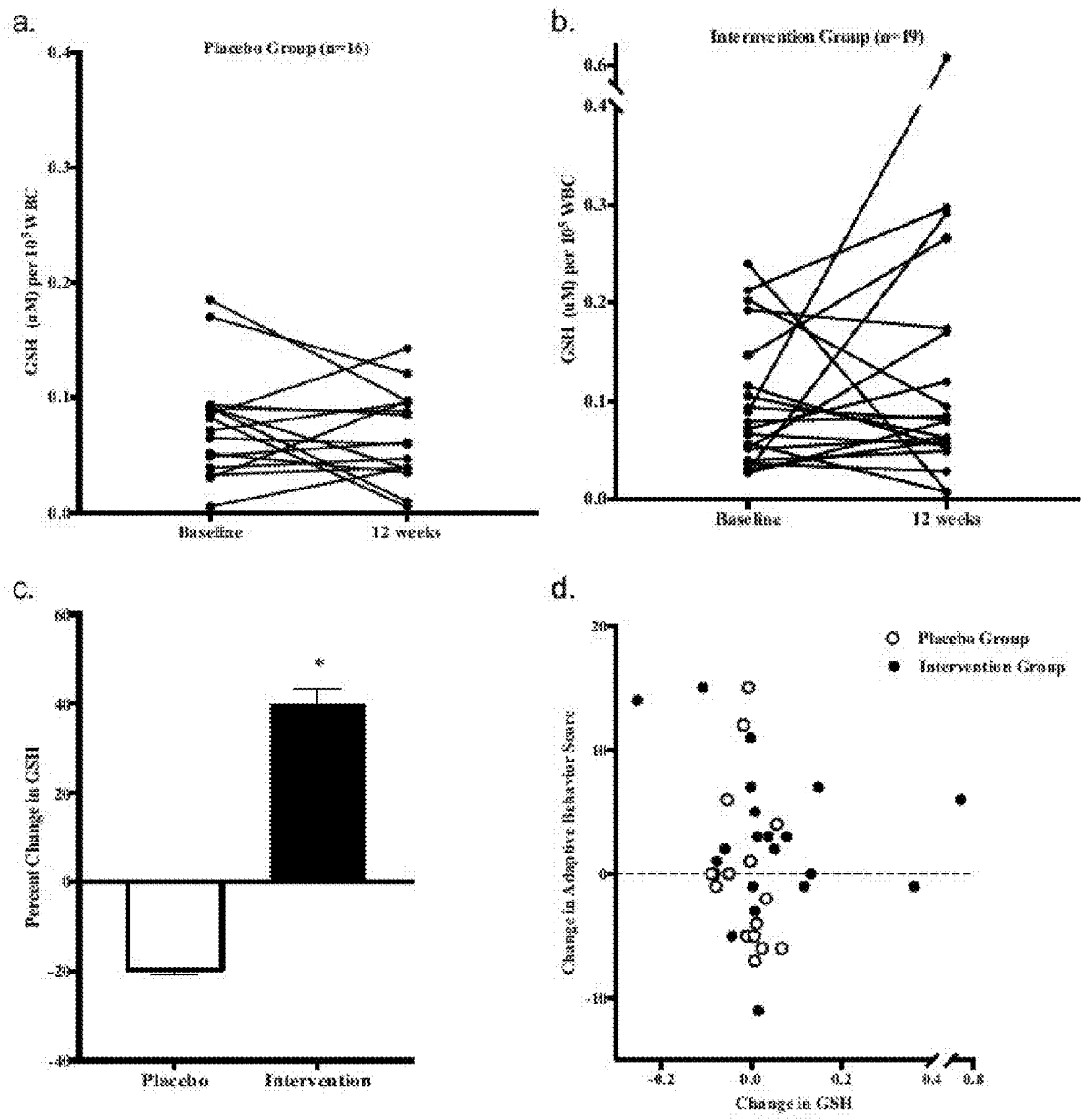
FIG. 4 shows scatterplots of individual subjects for reduced glutathione in a) Placebo Group (n=16) and b) intervention group (n=19). c) Percent change from baseline of reduced glutathione levels in placebo and intervention groups, where * denotes p-value<0.05 using one tail t-test. d) Change in adaptive behaviour score versus change in reduced glutathione levels for both groups, according to the study described in Example 1.

Higher levels of total and reduced glutathione were observed from baseline to follow-up in the CRWP group (FIG. 4). In contrast, no significant changes in the placebo group in total, reduced or oxidized glutathione levels were observed. Improvements in glutathione levels were also evident when looking at individual changes from baseline to follow-up in the CRWP group using scatterplots with connected lines (FIGS. 4A and 4B). After the 90-day supplementation, changes in both total (p=0.02) and reduced glutathione (p=0.04) in the CRWP were significantly higher compared to changes in the placebo group (p=0.04). Using the VABS-II, we analyzed changes in behavior versus changes in glutathione; however, behavior improvements observed using this assessment were not significantly correlated with changes in glutathione levels (FIG. 4D).

Analysis of Responders

Figure 5:
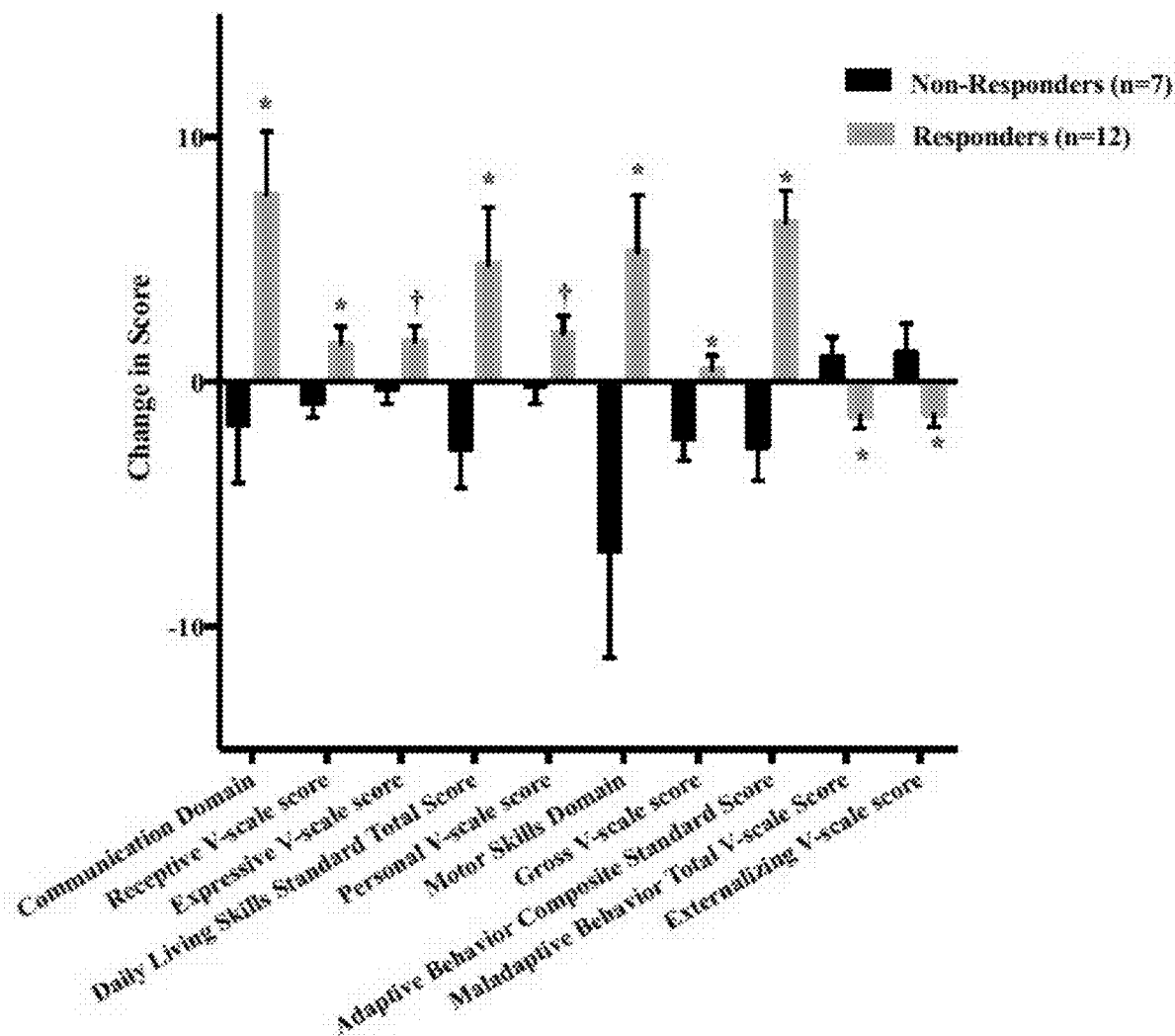
FIG. 5 shows change in Vineland Adaptive Behaviour Scale, $2^{nd}$ edition, scores in non-responders and responders, where * denotes a p-value<0.05, according to the study described in Example 1.

Since there were a significant number of subjects within the CRWP group which improved in adaptive behavior as measured by the VABS-II, common characteristics of those among this group of responders were explored. In this analysis, differences in the responses within the CRWP (to the supplement) and which variables were common among those in this group were identified. We observed that among those in the intervention (CRWP) group, there were several (60%) children that showed significant improvements in the VABS while others did not. Changes in more than 2 points or 1 standard deviation in the VABS-II composite scores were used to discriminate the responders. Twelve "responders" were identified out of the 19 that completed the behavioral assessments in the CRWP group versus only 5 out of 21 (those who completed behavior assessments) were identified as responders in placebo group (p=0.03). When comparing the responders from the CRWP group (n=12) to the non-responders in the same group (n=7), there was a significant difference in the age (p=0.03). The responders were significantly older (4.23±0.22 years) compared to non-responders (3.48±0.18 years). Moreover, the responder group did have significantly higher levels of total glutathione (p=0.01) and reduced glutathione (p=0.01) at baseline compared to the non-responder group (FIG. 5). However, no difference was found between the two groups when comparing changes in total, reduced and oxidized glutathione levels (responders p=0.05, non-responders p=0.06) (Table 4).

TABLE 4

Demographics and Glutathione Levels of Responders (n = 12) and Non-Responders (n = 7)

| Characteristic of Responders and Non-Responders from Intervention Group: | Responders (n = 12) | Non-responders (n = 7) | p- value |
| --- | --- | --- | --- |
| Age, (Mean + SEM) | 4.23 ± 0.22 | 3.48 ± 0.18 | 0.03* |
| Parent information (Mean + SEM) | | | |
| Paternal Age at birth (years) | 34.3 ± 3.84 | 39.5 ± 5.2 | 0.45 |
| Maternal Age at birth (years) | 33.1 ± 2.47 | 36.9 ± 3.0 | 0.35 |
| Baseline Glutathione Levels | | | |
| tGSH (nM/10*5 WBC) | 144.8 ± 21.4 | 65.6 ± 11.7 | 0.01* |
| GSH (nM/10*5 WBC) | 127.8 ± 19.8 | 51.3 ± 9.87 | 0.01* |
| Change in Glutathione Levels | | | |
| tGSH (nM/10*5 WBC) | 46.1 ± 60.8 | 64.9 ± 49.2 | 0.83 |
| GSH (nM/10*5 WBC) | 36.8 ± 56.1 | 41.7 ± 37.2 | 0.95 |

Figure 6:
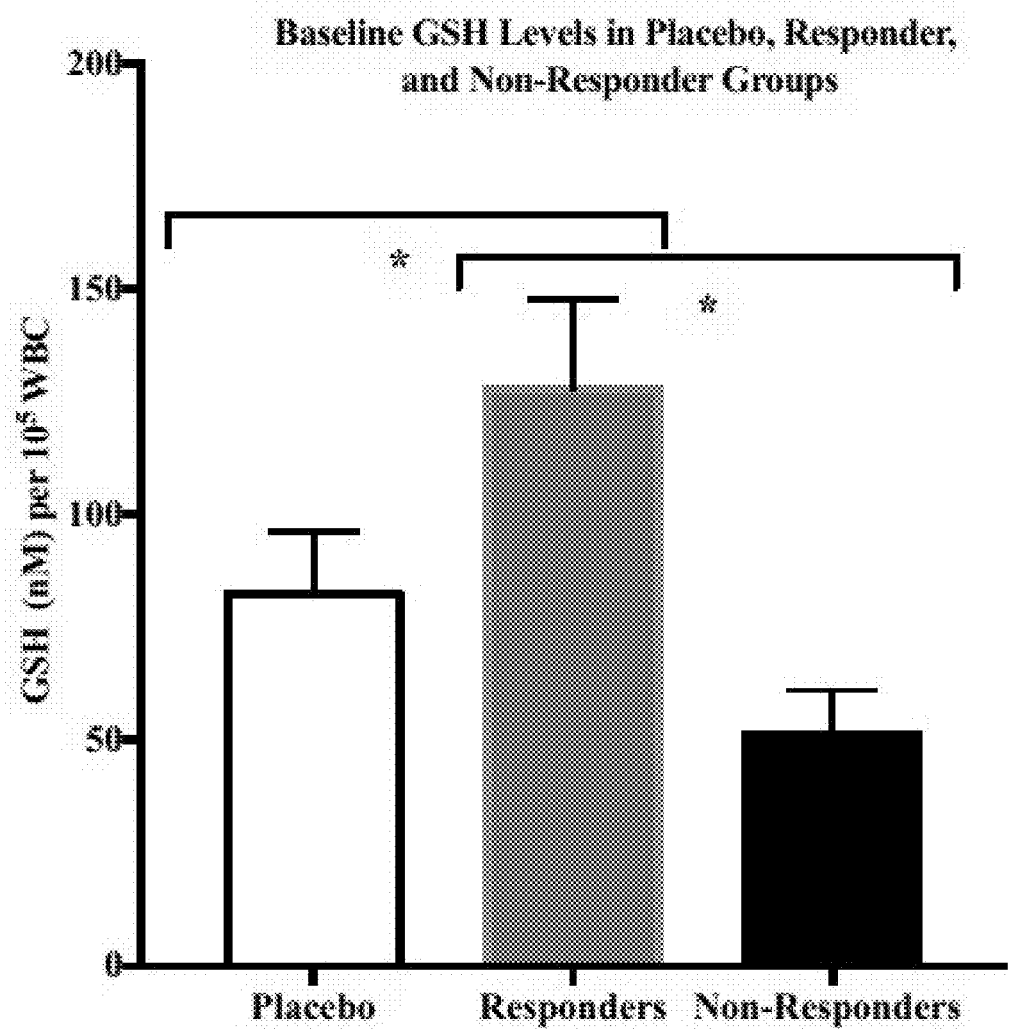
FIG. 6 shows intracellular GSH concentration at baseline across groups, where * indicates p<0.05, according to the study described in Example 1.

Further analysis of the VABS-II was used to compare the behavioral changes in the responders versus the non-responders among the intervention group (FIG. 6). The "responders" showed a much larger improvement in the given domains/sub-domains of the VABS-II such as: adaptive behavior composite score (p<0.0001, p=0.0003 compared to non-responders and placebo respectively), communication score (p=0.008, p=0.01 compared to non-responders on placebo respectively), receptive V-scale score (p=0.01 compared to non-responders), expressive v-scale score (p=0.03 compared to non-responders), daily living skills (p=0.008, p=0.007 compared to non-responders and placebo respectively), and personal v-scale score (p=0.03, p=0.004 compared to non-responders and placebo respectively) (Table 5). Responder improvements were also shown in socialization standard total (p=0.04, p=0.02 compared to non-responders and placebo respectively), play and leisure time (p=0.03, p=0.04 compared to non-responders and placebo respectively), coping skills (p=0.03, p=0.04 compared to non-responders and placebo respectively), motor skills standard total score (p=0.02 compared to non-responders), and gross motor score (p=0.01 compared to non-responders). Moreover, decreases in internalizing (p=0.04, p=0.0003 compared to non-responders and placebo respectively), externalizing (p=0.02, p=0.008 compared to non-responders and placebo respectively) and maladaptive behavior scores (p=0.01, p=0.003 compared to non-responders and placebo respectively) were also seen in the responders group showing a favorable effect (Table 5).

Secondary Outcomes

There were no serious adverse events reported in either treatment group. Table 6 details a list of all adverse events reported over the course of this study. Compliance was assessed by the weight of the canisters before and after treatments and did not show significant differences between the groups (90.5% in the placebo group versus 89.9% in the CRWP; p=0.91). Furthermore, there were more dropouts in the placebo group compared to the CRWP group. According to parents' diaries and records from the middle visit (Visit 5), nausea was mostly reported in the first weeks of the trial in each group but tended to improve as parents adapted their technique to reconstitute the supplement in powder with different juices/meals. There were also no significant changes in any of the complete blood count and comprehensive metabolic panel values obtained throughout study.

TABLE 5

Responders versus Non-Responders in Vineland Adaptive Behaviour Scale

| Vineland Adaptive Behavior Scale: | Non-Responders (n = 8) | Responders (n = 12) | p-value |
|---|---|---|---|
| Communication Standard Total Score | −1.71 ± 2.40 | 7.67 ± 2.55 | 0.02* |
| Receptive V-scale score | −0.86 ± 0.59 | 1.58 ± 0.69 | 0.02* |
| Expressive V-scale score | −0.29 ± 0.60 | 1.67 ± 0.63 | 0.02* |
| Written V-scale score | 0.29 ± 0.52 | 0.64 ± 0.47 | 0.63 |
| Daily Living Skills Standard Total Score | −2.7 ± 1.6 | 4.83 ± 2.31 | 0.03* |
| Personal V-scale score | −0.14 ± 0.77 | 2 ± 0.71 | 0.03* |
| Domestic V-scale score | −0.71 ± 0.60 | −0.08 ± 0.57 | 0.48 |
| Community V-scale score | −0.43 ± 0.62 | 0.33 ± 0.45 | 0.32 |
| Socialization Standard Total Score | −0.43 ± 2.17 | 6.67 ± 3.04 | 0.12 |
| Interpersonal Relationships V-scale score | 0.29 ± 0.57 | 0.83 ± 0.82 | 0.64 |
| Play and Leisure Time V-scale score | −0.43 ± 0.37 | 0.92 ± 0.58 | 0.12 |
| Coping Skills V-scale score | −0.15 ± 0.51 | 2.58 ± 1.18 | 0.11 |
| Motor Skills Standard Total Score | −6.86 ± 4.4 | 5.33 ± 2.32 | 0.02* |
| Gross V-scale score | −2.29 ± 0.92 | 0.5 ± 0.57 | 0.01* |
| Fine V-scale score | 0 ± 0.62 | 1.33 ± 0.54 | 0.14 |
| Adaptive Behavior Composite Standard Score | −2.63 ± 1.40 | 6.5 ± 1.32 | 0.01* |
| Maladaptive Behavior Total V-scale Score | 1 ± 0.84 | −1.4 ± 0.47 | 0.01* |
| Internalizing V-scale score | 0 ± 0.37 | −1.33 ± 0.64 | 0.18 |
| Externalizing V-scale score | 1.2 ± 1.20 | −1.33 ± 0.51 | 0.03* |

TABLE 6

Adverse Events Reported Over Course of the Study

| Adverse events, N (%): | Placebo (n = 19) | Intervention (n = 21) | p- value |
|---|---|---|---|
| Bronchitis/Cough/Respiratory Infection | 2 (8) | 4 (19) | 0.45 |
| Cold symptoms | 7 (29) | 9 (43) | 0.70 |
| Constipation | 3 (13) | 1 (5) | 0.25 |
| Diarrhea | 1 (4) | 4 (19) | 0.19 |
| Emesis/Nausea | 0 (0) | 7 (33) | 0.01 |
| Fever | 2 (8) | 4 (19) | 0.45 |

TABLE 6-continued

Adverse Events Reported Over Course of the Study

| Adverse events, N (%): | Placebo (n = 19) | Intervention (n = 21) | p- value |
|---|---|---|---|
| Rash | 0 (0) | 1 (5) | 0.34 |
| Other/Etc. | 3 (13) | 4 (19) | 0.77 |

Discussion

The heterogeneity of ASD can be observed in the neurologic, metabolic, and immunologic systems. Therefore, it is speculated to be a multi-factorial disorder, involving epigenetics, genetics and environmental factors. Oxidative stress may serve as a link between different systems affected in this condition. Oxidative stress occurs when there is an imbalance between reactive oxygen species (ROS) and antioxidant capacity. Glutathione, the major endogenous antioxidant, is the body's main defense against damage from ROS and is low in those with autism (Zoroglu et al. 2004; James et al. 2004, 2006, 2008; Kern and Jones 2006; Chauhan and Chauhan 2006; Geier and Kern 2009; Geier et al. 2010; Ghanizadeh et al. 2012; Chauhan et al. 2012). Metabolites in the transmethylation and transsulfuration pathways, which are responsible for the production of glutathione, are imbalanced in those with this disorder. Children with autism were found to have significant decreases in methionine levels and in the ratio of plasma S-adenosylmethionine (SAM) to S-adenosylhomocysteine (SAH) (SAM: SAH ratio), an index of methylation capacity (James et al. 2004; Rose et al. 2011; 2012).

Most importantly, subjects also had a decreased amount of total glutathione and reduced, or active form, glutathione. Cysteine, the rate limiting amino acid in glutathione synthesis, was significantly decreased relative to control children suggesting that glutathione synthesis was insufficient to maintain redox homeostasis in autism (James et al. 2004). These significant decreases in total and free plasma glutathione as well as the redox ratios (GSH:GSSG) in autistic children is of particular concern due to the importance of this system for normal cell function.

Although prior nutritional interventions addressing antioxidant capacity have been able to successfully improve glutathione levels, the association between these changes and autistic behavior has been less compelling. For example, N-acetylcysteine (NAC), which has a similar mechanism of action to the supplement utilized in this study, was effective at improving irritability in autistic children (Hardan et al. 2012). However, in a more recent study using NAC, glutathione production was increased but there was not significant improvement in social skills in youth with ASD (Wink et al. 2016). Other supplements, such as methylcobalamin, folic acid, folinic acid and combination treatments have also been investigated to improve antioxidant capacity and/or autism behaviors; these interventions are based upon abnormalities in the transmethylation/transsulfuration pathways (Bertoglio et al., 2010; Frye et al. 2013a; Hendren et al. 2016; Frye et al. 2013b; James et al., 2009; Adams and Holloway, 2004), and their effectiveness remains unclear. On the other hand, omega 3 fatty acids, vitamin C and sulforaphane have also been studied in those with this disorder targeting oxidative stress via different mechanisms of action with mixed results (Bent et al., 2014; 2011; Mankad et al. 2015; Politi et al. 2008; Singh et al. 2014; Voigt et al. 2014). Limited pharmacological alternatives that only target specific comorbid conditions are limited and with a significant burden of side effects; justifying the need for further studies utilizing complementary and alternative medicine (CAM) in the treatment of autism.

A nutritional supplement composed of cysteine rich whey protein isolate (CRWP) that serves as potent glutathione precursor, Immunocal®, is commercially available. Specific proteins in this supplement such as lactoferin, serum albumin, alpha lactalbumin and immunoglobulins, are rich in cysteine and cystine residues, which are bioavailable for cellular absorption and subsequent glutathione synthesis. In prior clinical trials, this CRWP was able to raise glutathione levels in those with obstructive lung disease (Lothian, Grey, Kimoff, and Lands, 2000), liver dysfunction in patients with chronic hepatitis B (Watanabe et al. 2000), healthy athletes (Lands, Grey, and Smountas 1999; 2013) and cystic fibrosis (Grey, Mohammed, Smountas, Bahlool, and Lands 2003). This cysteine-rich whey protein supplement was found to be safe and tolerable in a 6-week open label study in children with autism (Kern and Grannemann 2008; Oral Tolerability of Cysteine-Rich Whey Protein Isolate in Autism—A Pilot Study, JANA, 11(1), 2008, 36-41, described in the background section above).

In the present study, a double-blind placebo-controlled design was used to determine the effectiveness of a 90-day intervention with a nutritional supplement containing a cysteine rich whey protein isolate on autism core behavioral symptoms and glutathione levels in preschool children with autism. The present study also investigated whether improvements in intracellular glutathione correlated with behavioral changes. A comprehensive and age-specific behavioral assessment utilizing a total of eight different tests was used to assess which core areas of autism could be impacted with this intervention in children ages 3-5.

In part, the present studies sought to determine if supplementation with cysteine-rich whey protein isolate would improve behaviors and/or intracellular glutathione levels in children with autism aged 3-5 years old. A comprehensive behavioral assessment was utilized to fully evaluate the impact of this supplementation, making this approach unique at evaluating multiple behavioral aspects in this condition. Furthermore, a rice protein powder, which mimics the amount of protein obtained from whey, was used as placebo. The present results suggest a beneficial effect of such supplement on several aspects of autism behavior, as well as an improvement in antioxidant capacity demonstrated by the increased in glutathione levels.

Significant advancements were observed in both groups when comparing baseline to follow-up behavioral scores in CARS, SCQ, and ADI-R. It was expected that all children participating in this study would have some behavioral improvement, particularly because they had access to standard of care during the study consisting of preschool centers and therapies that provide special services to this population. However, when comparing the magnitude of changes between the two groups after the 3 months ($\Delta$ vs. $\Delta$), significant behavioral improvements with medium-large effect sizes were seen in the intervention group in the VABS-II assessment and its subdomains namely: adaptive behavior composite score, socialization and personal daily living skills as well as in the emotionally reactive portion of the CBCL. Randomized double-blind, placebo-controlled studies may be used to reveal accurate improvements with specific interventions. It is worth noting that children within the intervention group had to improve more than the placebo group in order to observe significant outcomes since their baseline values indicated they were more severely affected by this disorder.

In children with autism, several behavioral improvements have been associated with nutritional interventions. NAC supplementation was associated with a decrease in irritability using the Aberrant Behavior Checklist ABC and in repetitive behaviors using the Repetitive Behavior Scale-Revised (RBS-R) and Social Responsiveness Scale (SRS) assessments in a pilot study (Hardan et al. 2012). In contrast, Wink et al. (2016) found no behavioral improvements in a similar study design. Vitamin B6 supplementation was associated with positive changes in sleep and gastrointestinal issues in a randomized, double-blind, placebo controlled 3-month study in 20 children with autism using a parent-rated scale (Adams and Holloway, 2004). Other supplements closely related to the transmethylation and transsulfuration pathway were also associated with improved motor skills, in a case study (Moretti et al. 2005) and in multiple areas (Bertoglio et al. 2010) when focusing on a subgroup of subjects. In some ways, the present study relates to the results of Frye et al. (2013a), which showed significant increases in certain of the same VABS-II scores after supplementation with methylcobalamin plus folinic acid. Each study utilized clinician, parent or a combination of scales to assess changes in behavior. The fact that different studies use a variety of diverse scales and study designs to assess behavioral changes, makes it difficult to compare results with most previous studies using other nutritional interventions.

A total of 12 out of 20 (60%) children were recognized as responders to the intervention due to the greater than 2-point improvement in VABS-II. Recently, Chatham et al. (2017) showed that the minimal clinically-important difference in children with autism ranged from 2-3.75 points, supporting our approach to identify these children as "responders". Moreover, the fact that parents blinded to the intervention reported significant differences in their child's adaptive behavior (VAB-II) on scales assessing several affected domains plus daily living activities, is very powerful. Improvements in the VABS-II of 4-5 points were also noted in the Phase II clinical trial of balovaptan in autistic adults. Although measuring adaptive behavior was not a primary outcome of this clinical trial, the improvements in this assessment gained the FDA's breakthrough therapy label (Hoffmann-La Roche 2018). Since autism spectrum disorders encompasses a broad phenotype in terms of its behavioral presentation without a known etiology, it is expected that not all patients will respond equally to one intervention. Therefore, children diagnosed with autism and impaired behavior in areas that demonstrated significant improvements with this intervention, may be indicated as good candidates for such nutritional supplementation.

Others have found that targeting antioxidant capacity using different interventions such as methylcobalamin, folinic acid (Frye et al. 2013a; James et al. 2009) or n-acetylcysteine (Ghanizadeh and Moghimi-Sarani 2013; Hardan et al. 2012) may be beneficial in a subgroup of children with this condition. Previously, however, there were no genotypes or phenotypes associated with responders to these interventions. Clinicians and caregivers may significantly benefit from identifying patients that may potentially respond to such treatments. It is also possible that additive beneficial effects may be found when combining these therapies as in the case of methylcobalamin plus folinic acid (Frye et al. 2013a; James et al. 2009).

Significant improvements in glutathione levels of autistic children were confirmed in the present pilot study using a nutritional approach known to increase glutathione biosynthesis. As expected, children assigned to the supplement experienced a 40% significant increase in the reduced form of glutathione since this supplement provides a natural source of cysteine, the rate limiting step in glutathione biosynthesis, that will ultimately lead to increased intracellular levels.

Other interventions have demonstrated comparable glutathione increases to those in the present intervention group. The combination of methylcobalamin and folinic acid showed increases of 15% in total glutathione and 20% reduced glutathione respectively (Frye et al., 2013a), while NAC treatment has shown a 60% increase from baseline (Wink et al. 2016). The importance of targeting glutathione levels in this condition is relevant since significant difference in glutathione and its related metabolites have been found in plasma (James et al. 2004, 2006), white blood cells (Ghezzo et al. 2013; Melnyk et al. 2012) and post-mortem brains (Chauhan et al. 2012; Rose et al. 2012) of subjects with autism. This finding is also supported by several genetic variations seen in ASD patients related to the transmethylation/transsulfuration pathway where glutathione is one of the byproducts (James et al., 2004, 2006, 2008). A hypothesis that low glutathione levels are related to ASD symptoms may be partially supported by the fact that certain treatments targeting this deficiency have been shown to be efficacious at modifying certain behavioral symptoms in children with this condition (Frye et al. 2and 013a; Ghezzo et al. 2013).

The present studies additionally investigated the correlation between behavioral improvements and changes in glutathione intracellular concentrations. While the present inventors initially hypothesized that the magnitude of glutathione increases would be correlated with behavioral improvements as in other studies (Frye et al. 2013a; Hardan et al. 2012), the present studies found no correlation between changes in glutathione levels and improvement in the VABS-II. However, it is quite clear that both core areas in autism behaviors and antioxidant capacity were positively impacted by the present intervention. It may be that the benefit of the CRWP may not be limited to its efficacy at increasing antioxidant capacity, but its ability to improve overall health.

When examining the relationship between baseline glutathione levels, the responders (n=12) had significantly higher baseline concentrations of both total and reduced glutathione in comparison to baseline and the non-responders (n=8), suggesting that these subjects were closer to obtaining a threshold in their glutathione levels leading to positive changes in behavior. It is possible that children with lower baseline glutathione levels, may need a higher dose or a longer intervention to attain similar behavioral outcomes.

Evidence-based effective and safe interventions in ASD are highly sought after in order to ease some of the behavioral problems seen in this condition. The use of complementary and alternative medicine has been reported to be at around 74% in children with autism (Hanson et al. 2007; Lofthouse et al. 2012; Perrin et al. 2012; Rossignol et al. 2009). By avoiding traditional pharmacological treatments that may produce significant side effects, parents try to alleviate behavioral problems and associated comorbid conditions using alternative treatments. Therefore, there is a significant need to investigate the efficacy of complementary and alternative therapies and their tolerability in children with autism while also identifying those that respond to these interventions.

The experimental results described in this Example identify that nutritional intervention with a cysteine-rich whey protein isolate effectively improved glutathione levels in children with autism, ameliorated some behavioral domains impacted in ASD, and was well tolerated.

EXAMPLE 2

Whey Characteristics of Whey Protein Isolate Production

An example of whey protein isolate production is provided below for illustrative purposes intended for the person of skill in the art.

As will be understood, whey may be considered as a by-product of cheese or of casein manufacture. Whey typically contains soluble proteins of milk, so-called whey proteins. Cheese whey, for example, typically contains 5-8 g/l of proteins (N×6.38), among which β-lactoglobulin (β-lg) and α-lactalbumin (α-la) are the most abundant (accounting for 50-55% and 15-20% of total whey proteins, respectively) and bovine serum albumin (BSA), lactoferrin (LF) and immunoglobulins (IgG) are considered as minor whey proteins (accounting each for 3-5%). Whey may also comprise protein fragments or polypeptides such as so-called proteose-peptones (PP-4, PP-5, PP-8f) resulting from proteolysis of milk proteins by lactic starters in cheesemaking or by psychotropic bacteria during cold storage of raw milk. These proteinaceous compounds are not completely characterized, and their concentration in whey is highly variable. Finally, non-protein nitrogen (NPN) group may comprise a large number of molecules in whey, among which urea may account for 50-60%.

For illustrative purposes, Table 7 below provides some characteristics of some of the major proteins and polypeptides found in an exemplary whey sample (in this case, bovine sweet whey).

TABLE 7

Some Characteristics of Major Proteins and Polypeptides in an Exemplary Whey Sample

| Protein or polypeptide | Weight contribution (g/l) (approx.) | Molecular weight |
|---|---|---|
| β-lactoglobulin | 3.0 | 18 400 |
| α-lactalbumin | 1.2 | 14 200 |
| BSA | 0.3 | 69 000 |
| Lactoferrin | 0.2 | 77 000 |
| IgG | 0.2 | 160 000 |
| PP-3 | 0.6 | 22 000 |
| PP-5 |  | 14 300 |
| PP-8f |  | 4 100 |
| NPN | 1.6 |  |

In this example, whey protein isolate may be obtained from whey, such as the whey exemplified above in Table 7. As will be understood, process steps involved in the manufacture of whey protein isolate (WPI) may lead to compositional differences in terms of protein profile between whey protein isolates. Thus, the specific components and their abundance are not meant to be considered limiting in any manner. Factors influencing whey protein isolate characteristics may include, for example:

[1] Source of the whey proteins: For example, sweet- or acid- whey may be used as starting material for the manufacture of WPI;

[2] Pasteurization: For example, the proteins in cheese whey-derived ingredients may be submitted to two (2) pasteurization (i.e. 72-75° C.-12-16 sec.) treatments at a cheese plant where milk is pasteurized (Canada and US regulation) before cheesemaking, or at the ingredient manufacturing plant, or before transportation of drained whey to this plant, in order to reduce bacterial count before membrane processing or ion exchange chromatography; and

[3] Defatting: For example, centrifugal clarification is typically used to reduce the fat content of whey to 0.8-1.2%. However, an additional defatting step is often performed to further decrease the fat content to 0.3-0.5% in order to increase membrane separation performance or to prevent an irreversible fouling or clugging of ion-exchange resins with polar lipids. Defatting typically involves holding whey at 50-55° C. for 30 to 90 min. in order to promote aggregation of fat particles (optionally in the presence of added CaCl2). The product will thereafter be submitted to centrifugal separation or MF in order to remove the agglomerated material.

In this example, high-protein concentration (>90% dry basis) whey protein isolate may typically be prepared from whey such as that exemplified in Table 7 by either of two methods: membrane processing or ion-exchange chromatography. In membrane processing, microfiltration (MF) and/or ultrafiltration (UF) membranes may be used for concentrating whey. In ion-exchange chromatography, cationic- and/or anionic-exchange chromatography may be used to purify whey proteins.

In this example, obtained samples may be submitted to spray drying conditions. Where a substantially undenatured isolate is to be prepared, the obtained concentrated liquid may be, for example, sprayed in a hot air current (inlet T°: 180-200° C., outlet T°: 80-100° C.) circulating in a spray drying tower. A combination of dehydration and gravity may allow the collection of dry particles (4-8% humidity) at the bottom of the spray dryer. Estimates obtained from mathematical modeling of such drying processes suggest that the droplet temperature does not exceed about 80-85° C. during the few seconds used for dehydration, providing for an example of low impact spray drying which may not substantially denature whey protein.

As will be understood, ingredients having high-protein contents may generally be more difficult to rehydrate (possibly because of their low lactose and minerals content). For certain applications where rapid rehydration of the powder obtained from spray drying is desired, the powder may be submitted to agglomeration. Such steps may involve a final drying of the powder (from 12-15% to 4% humidity) on a fluid bed, generating agglomerated particles having better sinkability in water. In products containing fat (which is generally not the case for high protein ingredients), lecithin may be injected during fluid bed drying. Lecithin may cover fat droplets and improve their wettability. Instantization step(s) may also be used, although such steps are generally uncommon in the manufacture of high-protein ingredients.

As a result of the above steps, an example of a whey protein isolate may be prepared from the whey protein starting material exemplified in Table 7 above. It will be understood that this example is provided for illustrative and non-limiting purposes, and that many alternative, substituted, or modified whey protein sources and/or processing steps known to the person of skill in the art having regard to the teachings herein are also contemplated.

EXAMPLE 3

Behavioural Domain Improvements in Subjects with Autism

Example 1 above describes an extensive clinical study investigating the treatment of autism with an undenatured whey protein isolate (Immunocal®). Detailed analysis of the collected data was performed, allowing behavioural domains where treatment demonstrated a particularly notable improvement to be identified. As can be seen from Table 2, several specific behavioural indices were improved. In certain embodiments, methods as described herein may be used to improve, in particular, one or more behavioural traits in a subject which are assessed by one or more of the behavioural assessments in Table 2 for which an improvement was identified.

Table 8 below identifies examples of particular behavioural assessments and measures in which Immunocal® treatment in the study provided a notable improvement in scores.

TABLE 8

Behavioural Domains in which Treatment Provided Notable Improvement

| Behavioral Assessment: | Scores | Δ CRWP Group | Assessment/ Score Thresholds | Score Interpretation |
|---|---|---|---|---|
| CARS | Behavior T-score | −1.80 | 15-29.5 = minimal-no sx<br>30-36.5 = mild-mod sx<br>>37 = severe sx | Lower scores are better. |
| ADI-R | Reciprocal Social Interaction | −0.82 | >10, "Autism" | Lower scores are better. |
| | Total | −3.81 | No threshold for total | |
| SCQ | Communication score | −2.22 | >15 = Autism | Lower scores are better. |
| VABS-II | Adaptive Behavior Composite | 2.85 | Standard Scores M = 100, SD 15. Therefore, any score <85 is threshold for composite and domains. Sub-domains scores M = 15, SD = 3. Therefore, any score <12 is threshold. | Higher scores are better. |
| | Communication Domain | 2.07 | | |
| | Expressive Communication Subdomain | 0.57 | | |
| | Personal Daily Living Skills Subdomain | 1.05 | | |
| | Socialization Domain | 2.65 | | |
| | Coping Skills Subdomain | 0.75 | | |
| | Fine Motor Skills Subdomain | 0.37 | | |
| CBCL | Emotionally Reactive T-score | −4.51 | ≥65, Baseline Level<br>>73, Clinical Level. | Lower scores are better. |

Accordingly, experimental results suggest that undenatured whey protein isolate, such as Immunocal®, may be particularly useful in improving one or more behavioural traits assessed by one or more of: CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score, in a subject in need thereof having autism or ASD.

In summary, in Example 1 described above, significant increases in tGSH and GSH were noted in the Immunocal® treated group, and significant improvements were also seen in Vineland, CARS, SCQ, and ADI-R totals in the Immunocal® treated group. Using covariate analysis, significant improvements were seen as compared to placebo in Vineland Adaptive Behaviour Scores, which is regarded as one of the most sensitive behaviour tests. Children with very low GSH levels showed less improvement on Immunocal® compared to those with higher levels. Further, Immunocal® was well tolerated and did not show significant side effects in ASD children.

One or more illustrative embodiments have been described by way of example. It will be understood to persons skilled in the art that a number of variations and modifications can be made without departing from the scope of the invention as defined in the claims.

REFERENCES 1. http://medicalhomeinfo.org/health/Autism%20downloads/AutismAlarm.pdf, C., Autism Alarm. 2005, CDC.
2. Folstein, S. E. and B. Rosen-Sheidley, Genetics of autism: complex aetiology for a heterogeneous disorder. Nat Rev Genet, 2001. 2(12): p. 943-55.
3. Keller, F. and A. M. Persico, The neurobiological context of autism. Mol Neurobiol, 2003. 28(1): p. 1-22.
4. Hornig, M. and W. I. Lipkin, Infectious and immune factors in the pathogenesis of neurodevelopmental disorders: epidemiology, hypotheses, and animal models. Ment Retard Dev Disabil Res Rev, 2001. 7(3): p. 200-10.
5. Horvath, K. and J. A. Perman, Autistic disorder and gastrointestinal disease. Curr Opin Pediatr, 2002. 14(5): p. 583-7.
6. Krause, I., et al., Brief report: immune factors in autism: a critical review. J Autism Dev Disord, 2002. 32(4): p. 337-45.
7. Bauman, M. L. and T. L. Kemper, The neuropathology of the autism spectrum disorders: what have we learned? Novartis Found Symp, 2003. 251: p. 112-22; discussion 122-8, 281-97.
8. White, J. F., Intestinal pathophysiology in autism. Exp Biol Med (Maywood), 2003. 228(6): p. 639-49.
9. James, S. J., et al., Metabolic endophenotype and related genotypes are associated with oxidative stress in children with autism. Am J Med Genet B Neuropsychiatr Genet, 2006. 141(8): p. 947-56.
10. Schafer, F. Q. and G. R. Buettner, Redox environment of the cell as viewed through the redox state of the glutathione disulfide/glutathione couple. Free Radic Biol Med, 2001. 30(11): p. 1191-212.
11. Dickinson, D. A., et al., Cytoprotection against oxidative stress and the regulation of glutathione synthesis. Biol Chem, 2003. 384(4): p. 527-37.
12. Klatt, P. and S. Lamas, Regulation of protein function by S-glutathiolation in response to oxidative and nitrosative stress. Eur J Biochem, 2000. 267(16): p. 4928-44.
13. Dickinson, D. A. and H. J. Forman, Glutathione in defense and signaling: lessons from a small thiol. Ann N Y Acad Sci, 2002. 973: p. 488-504.
14. Deplancke, B. and H. R. Gaskins, Redox control of the transsulfuration and glutathione biosynthesis pathways. Curr Opin Clin Nutr Metab Care, 2002. 5(1): p. 85-92.
15. Pastore, A., et al., Analysis of glutathione: implication in redox and detoxification. Clin Chim Acta, 2003. 333(1): p. 19-39.
16. Hall, A. G., Review: The role of glutathione in the regulation of apoptosis. Eur J Clin Invest, 1999. 29(3): p. 238-45.
17. Griffith, O. W., Biologic and pharmacologic regulation of mammalian glutathione synthesis. Free Radic Biol Med, 1999. 27(9-10): p. 922-35.
18. Konstantareas, M. M., Autistic children exposed to simultaneous communication training: a follow-up. J Autism Dev Disord, 1987. 17(1): p. 115-31.
19. Zimmerman, A. W., et al., Cerebrospinal fluid and serum markers of inflammation in autism. Pediatr Neurol, 2005. 33(3): p. 195-201.
20. Jyonouchi, H., et al., Dysregulated innate immune responses in young children with autism spectrum disorders: their relationship to gastrointestinal symptoms and dietary intervention. Neuropsychobiology, 2005. 51(2): p. 77-85.
21. Yorbik, O., et al., Investigation of antioxidant enzymes in children with autistic disorder. Prostaglandins Leukot Essent Fatty Acids, 2002. 67(5): p. 341-3.
22. Chauhan, A., et al., Oxidative stress in autism: increased lipid peroxidation and reduced serum levels of ceruloplasmin and transferrin—the antioxidant proteins. Life Sci, 2004. 75(21): p. 2539-49.
23. Witschi, A., et al., The systemic availability of oral glutathione. Eur J Clin Pharmacol, 1992. 43(6): p. 667-9.
24. Flagg, E. W., et al., Dietary glutathione intake in humans and the relationship between intake and plasma total glutathione level. Nutr Cancer, 1994. 21(1): p. 33-46.
25. PDR (Physician's Desk Reference). 2008, Montvale, N.J.: Thomson Healthcare Inc.
26. Lands, L. C., V. L. Grey, and A. A. Smountas, Effect of supplementation with a cysteine donor on muscular performance. J Appl Physiol, 1999. 87(4): p. 1381-5.
27. Kern, J., Grannnemann B. D., Gutman, J. and Trivedi M., Oral Tolerability of Cysteine-Rich Whey Protein Isolate in Autism—A Pilot Study. JANA, 2008. 11(1): p. 36-41.
28. Diagnostic and Statistical Manual of Mental Disorders. 4th ed, ed. A.P. Association. 1994, Washington: American Psychiatric Press.
29. Le Couteur, A., Lord, C and Rutter, M., Autism Diagnostic Interview-Revised (ADI-R). Western Psychological Services, 2003.
30. Zimmerman, I., Steiner, V G and Pond, R E, Preschool Language Scale-4 (PLS-4). The Psychological Corporation 2002.
31. Rutter, M., Bailey, A, and Lord, C. Wester Psychological Services, Social Communication Questionnaire (SCQ). 2003.
32. Mullen, E. A. G. S., Mullen Scales of Early Learning. 1995.
33. Sparrow, S., Cicchetti, D V, and Balla, D A., Vineland Adaptive Behavior Scales, Second Edition. 2005.
34. Achenbach, T., Child Behavior Checklist for Children Ages 1½ to 5 (CBCL 1½-5 LDS) ASEBA, 2000.
35. NIH. Issues to Consider in Research with Children . . . [cited 2008 7/23/2008]; Available from: http://www.cc-.nih.gov/ccc/pedweb/pedsstaff/pedprocheck.pdf.
36. FDA. Conversion of GRAS Petition No. 1G0371 to a GRAS Notification for Whey Protein Isolate and Dairy Product Solids. 2000 February 2010]; Available from: http://www.accessdata.fda.gov/scripts/fcn/gras_notices/grn000037.pdf.
37. James S J, Rose S, Melnyk S, et al. Cellular and mitochondrial glutathione redox imbalance in lymphoblastoid cells derived from children with autism. FASEB J. 2009; 23(8):2374-2383. doi:10.1096/fj.08-128926.
38. Frye R E, Delatorre R, Taylor H, et al. Redox metabolism abnormalities in autistic children associated with mitochondrial disease. Transl Psychiatry. 2013; 3(6): e273. doi:10.1038/tp.2013.51.
39. Dickinson D a, Moellering D R, Iles K E, et al. Cytoprotection against oxidative stress and the regulation of glutathione synthesis. Biol Chem. 2003; 384(4):527-537. doi:10.1515/BC.2003.061.
40. Klatt P, Lamas S. Regulation of protein function by S-glutathiolation in response to oxidative and nitrosative stress. Eur J Biochem. 2000; 267(16):4928-4944. http://www.ncbi.nlm.nih.gov/pubmed/10931175.
41. Dickinson, D A. And Forman, H. J. (2002), Glutathione in defense and signaling. Annals of the New York Academy of Sciences. 2000:973: 488-504. doi:10.1111/j.1749-6632.2002.tb04690.x
42. Deplancke B, Gaskins H R. Redox control of the transsulfuration and glutathione biosynthesis pathways. Curr Opin Clin Nutr Metab Care. 2002; 1:85-92.
43. Achenbach, T. M. (1991). Manual for the Child Behavior Check-list/4-18. Journal of Abnormal Child Psychology, 15, 629-650.
44. Achenbach, T. M., & Rescorla, L. A. (2000). Child Behavior Checklist. Burlington, Vt.: ASEBA.
45. Adams, J. and H. C. (2004). Pilot study of a moderate dose multivitamin/mineral supplement for children with autistic spectrum disorder. J Altern Complement Med, 10(6), 1033-9. http://doi.org/10.1089/acm.2004.10.1033
46. Adams, J. B., Audhya, T., McDonough-Means, S., Rubin, R. a, Quig, D., Geis, E., . . . Lee, W. (2011). Nutritional and metabolic status of children with autism vs. neurotypical children, and the association with autism severity. Nutrition & Metabolism, 8(1), 34. http://doi.org/10.1186/1743-7075-8-34
47. Alabdali, A., Al-Ayadhi, L., & El-Ansary, A. (2014). Association of social and cognitive impairment and biomarkers in autism spectrum disorders. Journal of Neuroinflammation, 11, 4. http://doi.org/10.1186/1742-2094-11-4
48. American Psychiatric Association. (2013). Diagnostic and Statistical Manual of Mental Disorders. Arlington. http://doi.org/10.1176/appi.books.9780890425596.744053
49. Bent, S., Bertoglio, K., Ashwood, P., Bostrom, A., & Hendren, R. L. (2011). A Pilot Randomized Controlled Trial of Omega-3 Fatty Acids for Autism Spectrum Disorder. Journal of Autism and Developmental Disorders, 41(5), 545-554. http://doi.org/10.1007/s10803-010-1078-8
50. Bent, S., Hendren, R. L., Zandi, T., Law, K., Choi, J., & Widjaja, F. (2014). Internet-based, randomized, controlled trial of omega-3 fatty acids for hyperactivity in autism. J Am Acad Child Adolesc Psychiatry., 53. http://doi.org/10.1016/j.jaac.2014.01.018
51. Bertoglio, K., James, J. S., Deprey, L., Brule, N., & Hendren, R. L. (2010). Pilot study of the effect of methyl B12 treatment on behavioral and biomarker measures in children with autism. Journal of Alternative and Complementary Medicine, 16(5), 555-60. http://doi.org/10.1089/acm.2009.0177
52. Chatham, C. H., Taylor, K. I., Charman, T., Liogier D'ardhuy, X., Eule, E., Fedele, A., . . . Bolognani, F. (2017). Adaptive behavior in autism: Minimal clinically important differences on the Vineland-II. Autism Research: Official Journal of the International Society for Autism Research. http://doi.org/10.1002/aur.1874
53. Chauhan, A., Audhya, T., & Chauhan, V. (2012). Brain region-specific glutathione redox imbalance in autism. Neurochemical Research, 37(8), 1681-9. http://doi.org/10.1007/s11064-012-0775-4
54. Chauhan, A., & Chauhan, V. (2006). Oxidative stress in autism. Pathophysiology: The Official Journal of the International Society for Pathophysiology/ISP, 13(3), 171-81. http://doi.org/10.1016/j.pathophys.2006.05.007
55. Christensen, D. L., Baio, J., Braun, K. V. N., Bilder, D., Charles, J., Constantino, J. N., . . . Yeargin-Allsopp, M. (2016). Prevalence and Characteristics of Autism Spectrum Disorder Among Children Aged 8 Years—Autism and Developmental Disabilities Monitoring Network, 11 Sites, United States, 2012. Morbidity and Mortality Weekly Report. Surveillance Summaries, 65(3), 1-23. http://doi.org/10.15585/mmwr.ss6503a1
56. Frye, R E., Slattery, J., & Quadros, E. (2017). Folate metabolism abnormalities in autism: potential biomarkers. Biomarkers in Medicine. http://doi.org/10.2217/bmm-2017-0109
57. Frye, R. E., Melnyk, S., Fuchs, G., Reid, T., Jernigan, S., Pavliv, O., . . . James, S. J. (2013). Clinical Study Effectiveness of Methylcobalamin and Folinic Acid Treatment on Adaptive Behavior in Children with Autistic Disorder Is Related to Glutathione Redox Status.
58. Frye, R. E., Sequeira, J. M., Quadros, E. V, James, S. J., & Rossignol, D. a. (2013). Cerebral folate receptor autoantibodies in autism spectrum disorder. Molecular Psychiatry, 18(3), 369-81. http://doi.org/10.1038/mp.2011.175
59. Geier, D. A., & Jkerndfwairnet, J. K. K. (2009). A Prospective Study of Oxidative Stress Biomarkers in Autistic Disorders, 5(1), 2-10.
60. Geier, D. a, Audhya, T., Kern, J. K., & Geier, M. R. (2010). Blood mercury levels in autism spectrum disorder: Is there a threshold level? Acta Neurobiologiae Experimentalis, 70(2), 177-86. Retrieved from http://www.ncbi.nlm.nih.gov/pubmed/20628441
61. Ghanizadeh, A., & Derakhshan, N. (2012). N-acetylcysteine for treatment of autism, a case report. Journal of Research in Medical Sciences: The Official Journal of Isfahan University of Medical Sciences, 17(10), 985-7. Retrieved from http://www.pubmedcentral.nih.gov/articlerender.fcgi?artid=3698662&tool=pmcentrez&rendertype=abstract
62. Ghanizadeh, A., & Moghimi-Sarani, E. (2013). A randomized double blind placebo controlled clinical trial of N-Acetylcysteine added to risperidone for treating autistic disorders. BMC Psychiatry, 13(1), 196. http://doi.org/10.1186/1471-244X-13-196
63. Ghanizadeh, a, Akhondzadeh, S., Hormozi, M., Makarem, a, Abotorabi-Zarchi, M., & Firoozabadi, a. (2012). Glutathione-related factors and oxidative stress in autism, a review. Current Medicinal Chemistry, 19(23), 4000-5. Retrieved from http://www.ncbi.nlm.nih.gov/pubmed/22708999
64. Ghezzo, A., Visconti, P., Abruzzo, P. M., Bolotta, A., Ferreri, C., Gobbi, G., . . . Mazzanti, L. (2013). Oxidative Stress and Erythrocyte Membrane Alterations in Children with Autism: Correlation with Clinical Features. PloS One, 8(6), e66418. http://doi.org/10.1371/journal.pone.0066418
65. Grey, V., Mohammed, S. R., Smountas, A. a, Bahlool, R., & Lands, L. C. (2003). Improved glutathione status in young adult patients with cystic fibrosis supplemented with whey protein. Journal of Cystic Fibrosis: Official Journal of the European Cystic Fibrosis Society, 2(4), 195-8. http://doi.org/10.1016/S1569-1993 (03)00097-3
66. Hanson, E., Kalish, L. A., Bunce, E., Curtis, C., McDaniel, S., Ware, J., & Petry, J. (2007). Use of complementary and alternative medicine among children diagnosed with autism spectrum disorder. Journal of Autism and Developmental Disorders, 37(4), 628-636.
67. Hardan, A. Y., Fung, L. K., Libove, R. a, Obukhanych, T. V, Nair, S., Herzenberg, L. a, . . . Tirouvanziam, R. (2012). A randomized controlled pilot trial of oral N-acetylcysteine in children with autism. Biological Psychiatry, 71(11), 956-61. http://doi.org/10.1016/j.biopsych.2012.01.014
68. Hendren, R., James, J. S., Widjaja, F., & Brittany, Rosenblatt Abram, and B. S. (2016). Randomized, Placebo-Controlled Trial of Methyl B12 for Children with Autism. Journal of Child and Adolescent Psychopharmacology, 26(9). http://doi.org/10.1089/cap.2015.0159
69. Immunocal. (2013). In Physician's Desk Reference.
70. James, S. J., Cutler, P., Melnyk, S., Jernigan, S., Janak, L., Gaylor, D. W., & Neubrander, J. a. (2004). Metabolic biomarkers of increased oxidative stress and impaired methylation capacity in children with autism. The American Journal of Clinical Nutrition, 80(6), 1611-7. Retrieved from http://www.ncbi.nlm.nih.gov/pubmed/15585776
71. James, S. J., Jill James, S., Melnyk, S., Jernigan, S., Hubanks, A., Rose, S., & Gaylor, D. W. (2008). Abnormal transmethylation/transsulfuration metabolism and DNA hypomethylation among parents of children with autism. Journal of Autism and Developmental Disorders, 38(10), 1966-75. http://doi.org/10.1007/s10803-008-0591-5
72. James, S. J., Melnyk, S., Fuchs, G., Reid, T., Jernigan, S., Pavliv, O., . . . Gaylor, D. W. (2009). Efficacy of methylcobalamin and folinic acid treatment on glutathione redox status in children with autism 1-3, 425-430. http://doi.org/10.3945/ajcn.2008.26615.Am
73. James, S. J., Melnyk, S., Jernigan, S., Cleves, M. a, Halsted, C. H., Wong, D. H., . . . Gaylor, D. W. (2006). Metabolic endophenotype and related genotypes are associated with oxidative stress in children with autism. American Journal of Medical Genetics. Part B, Neuropsychiatric Genetics: The Official Publication of the International Society of Psychiatric Genetics, 141B(8), 947-56. http://doi.org/10.1002/ajmg.b.30366
74. Kern, J., & Grannemann, B. (2008). Oral tolerability of cysteine-rich whey protein isolate in autism—a pilot study. J Am Nutraceut . . . , 11(1), 36-41. Retrieved from http://forums.immunolead.com/post?id=2254077
75. Kern, J. K., & Jones, A. M. (2006). Evidence of toxicity, oxidative stress, and neuronal insult in autism. Journal of Toxicology and Environmental Health. Part B, Critical Reviews, 9(6), 485-99. http://doi.org/10.1080/10937400600882079
76. Lands, L. C., Grey, V. L., & Smountas, A. A. (2013). Effect of supplementation with a cysteine donor on muscular performance Effect of supplementation with a cysteine donor on muscular performance, 1381-1385.
77. Lands, L. C., Grey, V. L., & Smountas, a a. (1999). Effect of supplementation with a cysteine donor on muscular performance. Journal of Applied Physiology, 87(4), 1381-1385.
78. Lofthouse, N., Hendren, R., Hurt, E., Arnold, L. E., & Butter, E. (2012). A Review of Complementary and Alternative Treatments for Autism Spectrum Disorders. Autism Research and Treatment, 2012, 1-21. http://doi.org/10.1155/2012/870391
79. Loke, Y. J., Hannan, A. J., & Craig, J. M. (2015). The Role of Epigenetic Change in Autism Spectrum Disorders. Frontiers in Neurology, 6(May), 107. http://doi.org/10.3389/fneur.2015.00107
80. Lord, C., Le Couteur, A., & Rutter, M. (1994). Autism Diagnostic Interview-Revised: A Revised Version of a Diagnostic Interview for Caregivers of Individuals with Possible Pervasive Developmental Disorders. Journal of Autism and Developmental Disorders, 24(5), 659-685.
81. Lord, C., Risi, S., Lambrecht, L., Cook, E. H., Leventhal, B. L., & DiLavore, P. C. (2000). The autism diagnostic observation schedule-generic: a standard measure of social and communication deficits associated with the spectrum of autism. J Autism Dev Disord., 30. http://doi.org/10.1023/A:1005592401947
82. Lord, C., Rutter, M., Goode, S., Heemsbergen, J., Jordan, H., Mawhood, L., & Schopler, E. (1989). Austism diagnostic observation schedule: A standardized observation of communicative and social behavior. Journal of Autism and Developmental Disorders, 19(2), 185-212. http://doi.org/10.1007/BF02211841
83. Lothian, B., Grey, V., Kimoff, R. J., & Lands, L. C. (2000). Treatment of obstructive airway disease with a cysteine donor protein supplement: a case report. Chest, 117(3), 914-6. Retrieved from http://www.ncbi.nlm.nih.gov/pubmed/10713031
84. Mankad, D., Dupuis, A., Smile, S., Roberts, W., Brian, J., Lui, T., . . . Anagnostou, E. (2015). A randomized, placebo controlled trial of omega-3 fatty acids in the treatment of young children with autism. Molecular Autism, 6(1), 18. http://doi.org/10.1186/s13229-015-0010-7
85. Manohari, S. M., Raman, V., & Ashok, M. V. (2013). Use of Vineland Adaptive Behavior Scales-II in Children with Autism—An Indian Experience. Journal of Indian Association for Children and Adolescent Mental Health, 9(1), 5-12.
86. Melnyk, S., Fuchs, G. J., Schulz, E., Lopez, M., Kahler, S. G., Fussell, J. J., . . . James, S. J. (2012). Metabolic imbalance associated with methylation dysregulation and oxidative damage in children with autism. Journal of Autism and Developmental Disorders, 42(3), 367-77. http://doi.org/10.1007/s10803-011-1260-7
87. Moretti, P., Sahoo, T., Hyland, K., Bottiglieri, T., Peters, S., Gaudio, D., . . . Scaglia, F. (n.d.). Cerebral folate deficiency with developmental delay, autism, and response to folinic acid, 3-5.
88. Mullen, E. M. (1995). Mullen Scales of Early Learning (AGS). Circle Pines, Minn.: American Guidance Service Inc.
89. Perrin, J. M., Coury, D. L., Hyman, S. L., Cole, L., Reynolds, A. M., & Clemons, T. (2012). Complementary and Alternative Medicine Use in a Large Pediatric Autism Sample. Pediatrics, 130(Supplement 2), S77S82. http://doi.org/10.1542/peds.2012-0900E
90. Politi, P., Cena, H., Comelli, M., Marrone, G., Allegri, C., & Emanuele, E. (2008). Behavioral effects of omega-3 fatty acid supplementation in young adults with severe autism: an open label study. Arch Med Res., 39. http://doi.org/10.1016/j.arcmed.2008.06.005
91. Rose, S., Melnyk, S., Pavliv, O., Bai, S., Nick, T. G., Frye, R. E., & James, S. J. (2012). Evidence of oxidative damage and inflammation associated with low glutathione redox status in the autism brain. Translational Psychiatry, 2(7), e134. http://doi.org/10.1038/tp.2012.61
92. Rose, S., Melnyk, S., Trusty, T. a, Pavliv, O., Seidel, L., Li, J., . . . James, S. J. (2011). Intracellular and extracellular redox status and free radical generation in primary immune cells from children with autism. Autism Research and Treatment, 2012, 986519. http://doi.org/10.1155/2012/986519

93. Rossignol, D. A. (2009). Novel and emerging treatments for autism spectrum disorders: a systematic review. Annals of Clinical Psychiatry: Official Journal of the American Academy of Clinical Psychiatrists, 21(4), 213-236.

94. Rutter Bailey, A., & Lord, C., M. (2003). Social Communication Questionnaire. Los Angeles, Calif.

95. Schopler, E., Reichler, R. J., DeVellis, R. F., & Daly, K. (1980). Toward objective classification of childhood autism: Childhood Autism Rating Scale (CARS). Journal of Autism and Developmental Disorders, 10(1), 91-103.

96. Singh, K., Connors, S. L., Macklin, E. a, Smith, K. D., Fahey, J. W., Talalay, P., & Zimmerman, A. W. (2014). Sulforaphane treatment of autism spectrum disorder (ASD). Proceedings of the National Academy of Sciences of the United States of America, 111(43), 15550-5. http://doi.org/10.1073/pnas.1416940111

97. Sparrow, S., Balla, D., & Cicchetti, D. (1984). Vineland Adaptive Behavior Scales. Circle Pines, Minn.: American Guidance Service Inc.

98. Tietze, F. (1969). Enzymatic Method for Quantitative Determination of Nanogram Amounts of Total and Oxidized Glutathione: Applications to Mammalian Blood and Other Tissues. Analytical Biochemistry, 27, 502-522.

99. Voigt, R. G., Mellon, M. W., Katusic, S. K., Weaver, A. L., Matern, D., Mellon, B., . . . Barbaresi, W. J. (2014). Dietary docosahexaenoic acid supplementation in children with autism. Journal of Pediatric Gastroenterology and Nutrition, 58(6), 715-722.

100. Volden, J., Smith, I. M., Szatmari, P., Bryson, S., Fombonne, E., Mirenda, P., . . . Thompson, A. (2011). Using the Preschool Language Scale-IV to Characterize Language in Preschoolers with ASD. Am J Speech Lang Pathol, 20(August), 200-208. http://doi.org/1058-0360_2011_10-0035 [pii]10.1044/1058-0360(2011/10-0035)

101. Watanabe, A., Okada, K., Shimizu, Y., Wakabayashi, H., Higuchi, K., Niiya, K., . . . Kohri, H. (2000). Nutritional therapy of chronic hepatitis by whey protein (non-heated). Journal of Medicine, 31(5-6), 283-302.

102. Wink, L. K., Adams, R., Wang, Z., Klaunig, J. E., Plawecki, M. H., Posey, D. J., . . . Erickson, C. A. (2016). A randomized placebo-controlled pilot study of N-acetylcysteine in youth with autism spectrum disorder. Molecular Autism, 7, 26. http://doi.org/10.1186/s13229-016-0088-6

103. Zoroglu, S. S., Armutcu, F., Ozen, S., Gurel, A., Sivasli, E., Yetkin, O., & Meram, I. (2004). Increased oxidative stress and altered activities of erythrocyte free radical scavenging enzymes in autism. European Archive of Psychiatry Clinical Neuroscience, 254, 143-147. http://doi.org/10.1007/s00406-004-0456-7

104. Roche, H.-L. (2018). A Study of RG7314 to Investigate Efficacy and Safety in Individuals With Autism Spectrum Disorders (ASD). https://clinicaltrials.gov/ct2 (Id. No: NCT0179344). Accessed 13 May 2018.

These references, and those cited elsewhere in the specification, are hereby incorporated by reference in their entirety.

What is claimed is:

1. A method for testing, treating and measuring an improvement in one or more behavioral traits of a subject with Autism or Autism Spectrum Disorder (ASD), said method comprising:
    scheduling 8 separate visits with a health care provider for the subject and performing the following steps at each respective scheduled visit:
        visit 1 comprises performing an initial assessment of the subject, the initial assessment consisting of receiving current drug/supplement intake information from the subject, wherein the subject is 4.23+/−0.22 years of age;
        visit 2 comprises obtaining 4 blood samples from the subject and determining the level of oxidative stress biomarkers, liver function, kidney function and blood cell count; the oxidative stress biomarkers comprising intracellular glutathione levels;
        visits 3 and 4 collectively comprise performing 8 behavioral assessments, said visits 3 and 4 each lasting an average of 2 hours and being performed within a 15 day window and no later than 15 days after visit 2; the behavioral assessments consisting of 1) Autism Diagnostic Observation Schedule (ADOS), 2) Childhood Autism Rating Scale (CARS), 3) Autism Diagnostic Interview-Revised (ADI-R), 4) Pre-school Language Scale-Fifth Edition (PLS-5), 5) Social Communication Questionnaire (SCQ), 6) Mullen Scales of Early Learning (MSEL), 7) Vineland Adaptive Behavior Scale, Second Addition (VABS-II) and 8) Child Behavior Checklist 1½-5 LDS (CNCL);
        visit 5 comprises recording adverse events about 6-7 weeks following visit 4, the adverse events selected from the group comprising bronchitis, cough, respiratory infection, cold symptoms, constipation, diarrhea, emesis, nausea, fever and rash;
        visits 6 and 7 collectively comprise re-performing the 8 behavioral assessments at 12 weeks following visit 4, said visits 6 and 7 each lasting an average of 2 hours and performed within a 15 day window, the assessments performed by the same clinical psychologists who performed the 8 behavioral assessments in weeks 3 and 4, and in the same sequence as performed in weeks 3 and 4;
        visit 8 comprises obtaining a further 4 blood samples to separately assess oxidative stress biomarkers, liver function, kidney function and blood cell count, the oxidative stress biomarkers comprising a second intracellular glutathione level measurement, wherein visit 8 is scheduled no later than 7 days after visit 7;
    administering a composition comprising whey protein isolate and/or whey protein concentrate to the subject as a treatment beginning at the end of visit 4, in an amount of 0.5 grams/kg for subjects under 20 kg or 10 g for subjects 20 kg and over, and lasting for at least 90 days; and
    measuring an improvement in the one or more behavioral traits of the subject as assessed by the Vinland Adaptive Behavior II Composite Scale; wherein the one or more behavioral traits comprise socialization, domestic daily living skills, maladaptive behavior and internalization as determined by the socialization domain, daily living skills domain, maladaptive behavior domain and internalizing subdomain of the Vinland Adaptive Behavior II Composite Scale, respectively.

2. The method according to claim 1, wherein the whey protein isolate and/or whey protein concentrate is substantially undenatured.

3. The method according to claim 1, wherein the Autism Spectrum Disorder (ASD) comprises autism, Asperger syndrome, pervasive developmental disorder not otherwise specified (PDD-NOS), Childhood Disintegrative Disorder, syndromic autism, autism of known etiology, fragile X syndrome, PTEN macrocephaly syndrome, RETT syndrome, tuberous sclerosis complex, Timothy syndrome, or Joubert syndrome.

4. The method according to claim 1, wherein treatment with the whey protein isolate and/or whey protein concentrate increases a tGSH level, a GSH level, or both, in the subject.

* * * * *